United States Patent [19]
Leet

[11] Patent Number: 6,000,828
[45] Date of Patent: Dec. 14, 1999

[54] METHOD OF IMPROVING DRUG TREATMENT

[75] Inventor: Larry Leet, Terrebone, Oreg.

[73] Assignee: Power Med Incorporated, Bend, Oreg.

[21] Appl. No.: 08/917,647

[22] Filed: Aug. 22, 1997

[51] Int. Cl.⁶ .............................................. G06F 159/00
[52] U.S. Cl. ........................................................ 364/401
[58] Field of Search .................................. 600/300, 301; 128/920, 923; 705/2, 3; 235/375

[56] References Cited

U.S. PATENT DOCUMENTS

| | | |
|---|---|---|
| 4,667,292 | 5/1987 | Mohlenbrock et al. . |
| 4,847,764 | 7/1989 | Halvorson . |
| 5,018,067 | 5/1991 | Mohlenbrock et al. . |
| 5,225,976 | 7/1993 | Tawil . |
| 5,301,105 | 4/1994 | Cummings, Jr. . |
| 5,483,443 | 1/1996 | Milstein et al. . |
| 5,550,734 | 8/1996 | Tarter et al. . |
| 5,551,022 | 8/1996 | Tariq et al. . |
| 5,557,514 | 9/1996 | Seare et al. . |
| 5,724,580 | 3/1998 | Levin et al. ............................ 707/104 |
| 5,778,345 | 7/1998 | McCartney .................................. 705/2 |

OTHER PUBLICATIONS

Basskin, L, "How to Use Decision Analysis to Solve Pharmacoeconomic Problems," *Formulary*; 32:619–628 (Jun. 1997).

Davis, NM, "Your New Computer System Must Help Prevent Medication Errors," *Hospital Pharmacy*; 32, No. 4:457, 511 (1997).

Nold, EG, "Trends in Health Information Systems Technology," *Am J Health–Syst Pharm*; 54:269–284 (Feb. 1997).

Slezak, M, "Programming Pharmacy's Future," *American Druggist*; 24–30 (Oct. 1995).

"Collaborative Outlines Strategies for Reducing Medication Errors," *Formulary*; 32:575 (Jun. 1997).

"Standards, Intents, and Examples for Medication Use," *Comprehensive Accreditation Manual for Hospitals: The Official Handbook*; (Aug. 1997).

*Primary Examiner*—George Manuel
*Attorney, Agent, or Firm*—Klarquist Sparkman Campbell Leigh & Whinston, LLP

[57] ABSTRACT

A computer implemented method and system for improving drug treatment of patients in local communities by providing drug treatment protocols for particular disease states, such as Diagnosis Related Group (DRG) classifications. The protocol contains ranked recommendations for drug treatments of the disease state, and the computer system collects information about the risks and benefits of the drug treatments. The information collected about the treatments is used to modify the rankings of the drug treatments in the protocol. In one specific embodiment of the system, where the disease state has a microbial etiology and the treatments are antimicrobial drugs, the emergence of drug resistance is quickly detected by determining the percentage of microbial isolates that are found to be resistant to antimicrobial therapy in the community where the therapy is being provided (such as a community hospital or city-wide health care system). An increase in the percentage of resistant isolates produces a re-ranking of recommended drug therapies to avoid further use of the drug to which resistance has developed, and helps quickly introduce more effective drugs that will improve the effectiveness and lower the cost of treatment. In yet other embodiments, a sum of medication (e.g. dosing) errors and adverse effects (e.g. allergic reactions) are tracked by the system to identify drugs that are poorly tolerated in particular populations served by the hospital where the treatment is being provided. Data is collected about the safety and effectiveness of all types of drug therapies in the community being served, and this data is used to modify the drug protocols.

31 Claims, 4 Drawing Sheets

FIG. 2  Data Flow - Hospital Environment

METHOD OF IMPROVING DRUG TREATMENT

FIELD OF THE INVENTION

The present invention concerns data processing systems for health care management, and is particularly directed to reducing health care costs by improving drug therapies. More specifically, the invention concerns improved data processing systems for tracking the cost, effectiveness and safety of drug therapies, and modifying recommended treatments in response to information gathered by the system.

BACKGROUND OF THE INVENTION

General Discussion of the Background

In recent years, there has been an ever increasing emphasis on improving the rational use of medical treatments to help reduce health care costs and enhance the quality of medical care. Previous efforts to manage health care, however, have often included retrospective approaches in which individual patient files were laboriously reviewed to determine the appropriateness of medical care a patient received. Such retrospective analyses can be assisted by categorization of diseases into Diagnosis Related Groups (DRGs), or International Classification of Disease (ICD) codes, which exhaustively classify illnesses and provide a statistical estimate of the acceptable cost of treating a particular medical condition.

Several automated systems have previously been proposed to help improve the effectiveness and reduce the cost of medical care. U.S. Pat. No. 5,583,758, for example, discloses a computer system in which a proposed treatment for a disease is entered into a computer, and the proposed treatment is compared to an approved treatment. If the proposed treatment differs from the approved treatment, the user is notified that specialist review is required to implement the proposed treatment.

In U.S. Pat. No. 5,018,067 a computer system is disclosed which calculates the severity of a patient's illness (based on the same criteria used for a DRG classification), and compares patient outcomes for patients having illnesses of similar acuity. The cost performance of a physician or hospital can then be determined by comparing the health care provider's actual costs incurred to an expected expense for treating a disease in the DRG classification. The computer system can also detect a changing diagnosis, which may indicate an improper initial diagnosis or treatment. This information provides a tool for monitoring physician and hospital performance.

U.S. Pat. No. 5,557,514 discloses a computer system for analyzing historical medical provider billings to establish a normative utilization profile. An individual provider's utilization profile is compared with a normative profile, to identify medical providers who provide treatments that do not fall within statistically established treatment patterns or profiles.

Efforts have also been made to provide laboratory information in a format that increases the efficiency of physicians who need to interpret the data to recommend a treatment. For example, U.S. Pat. No. 5,551,022 describes a computer implemented nodal tree structure for storing, consolidating and displaying microbiological laboratory results. This nodal structure allows the results of multiple microbiological tests to be consolidated and displayed in a matrix that facilitates the selection of appropriate antibiotic treatment.

Although these systems have used computers in an attempt to collect information about health care delivery, and provide information to a physician or other health care provider, these systems all assume that the ideal treatment is relatively fixed. This concept has resulted in the establishment of "formularies" at many hospitals, which provide a rigid list of available drugs (usually based on the cost of the drugs). This formulary approach is contrary to the realities of medicine, in which treatments evolve (increasingly quickly) as the pace of medical research advances. The fixed nature of recommended treatments also ignores the fact that diseases in different geographic locales are actually changed by the treatments selected, and that treatments are often more successful with certain ethnic and racial groups than with others.

An example of this problem is that bacteria develop resistance to antibiotic treatment. Hence antimicrobial treatment guidelines embedded in a computer program or hospital formulary can actually worsen a medical outcome by forcing physicians to overtreat with a particular antibiotic, against which microbial resistance is therefore developed. Moreover, once resistance develops, the recommended treatments suggested by the system can be dangerous, because they may have become ineffective. In addition, continuing to treat with the recommended antibiotic will only increase the development of resistance against that drug, and make it more difficult to treat subsequent patients who are infected with that microbial pathogen.

A related problem is that recommendations for pharmaceutical treatment are typically provided in national guidelines each year, based on statistical information gathered throughout the country. This approach has ignored the local nature of many diseases. Antibiotic resistance, for example, develops locally and spreads nationally, hence national guidelines may be inappropriate for a particular community. The long periods of time that elapse between the issuance of the guidelines also permits patterns of antibiotic resistance to become well established. This delay also means that clinicians who follow the national guidelines may be empirically selecting less than optimal initial antibiotic treatment for a disease pending the outcome of laboratory culture and sensitivity studies. Selection of an initial inappropriate empirical treatment can increase the length of stay of a patient in a hospital, which in turn increases health care expenditures. Hence existing approaches to treating infectious diseases can increase the cost of health care by perpetuating treatments that may no longer be optimally effective.

Yet another problem with drug treatment is that national recommendations for therapy may be inappropriate for certain subpopulations of patients. A population served by a particular hospital may have a large percentage of elderly patients, or patients of a particular race or ethnic group, who do not react well to a particular medication. The classic example of such an intolerance is the toxicity of primaquine (an anti-malarial agent) in blacks, Sardinians, Sephardic Jews, Greeks and Iranians. At the present time there is no mechanism for identifying optimal pharmaceutical treatments for such subpopulations of patients, and providing the optimal pharmaceutical intervention. There are few systems in place for identifying drugs that work best with subpopulations within a restricted geographic area, such as a state, city, or a particular hospital or health care system.

Drug studies are frequently performed to analyze the effectiveness of drugs, but such studies are often limited to test subjects of a particular race or gender. Such studies ignore the diversity of subpopulations of patients throughout the country, and sometimes cause inadequate or inappropriate treatments to be provided. This problem has become particularly acute now that hospitals and other health service centers are providing strict guidelines about the drugs that can be prescribed for patients who have particular diseases. Many of these recommendations are based solely on the purchase price of the drug, while ignoring other cost factors such as side-effects and medication errors that can complicate treatment and increase its actual cost.

SUMMARY OF THE INVENTION

It is accordingly an object of this invention to provide a computer operated system in which recommended drug treatments are allowed to evolve in response to changing medical information, side effects encountered, and patterns of disease resistance to recommended treatments.

It is also an object of the invention to provide such a system that can be used to evaluate drug treatments, provide information about the success of those treatments, and help improve drug treatments in the community in which the treatment is being provided.

A more specific object of the invention is to detect emerging patterns of microbial drug resistance in a community, and alter patterns of antimicrobial prescribing to reduce microbial evolutionary pressures that produce resistant organisms.

The foregoing objects are achieved by a computer system for improving drug treatment for a disease condition, in which is stored a first data field containing a diagnosis code (such as a Diagnosis Related Group) that is used as a key to access a plurality of disease conditions. Each diagnosis code corresponds to a particular disease condition. The diagnosis code is used as a key to access other information about the cause and treatments of the disease. A second data field of recommended treatments is indexed for each particular disease condition, and the recommended treatments are stored in a ranked order. A clinical outcome of an actual treatment selected for each patient is also recorded in memory. The recommended treatments for each particular disease condition are modified based on the data collected about the clinical outcome of recommended treatments.

In particularly disclosed embodiments, the recommended treatment comprises administering a drug, and the method further comprises displaying comparative costs, in association with the recommended treatments. The comparative costs can be based on the cost per unit dose of drugs that are included in the recommended treatments, and patient specific parameters (such as weight or body surface area) from which a predicted total required number of unit dosages of the drug are calculated. The projected cost of administering each of the recommended treatments is calculated from the cost per unit dosage and the predicted total required number of unit doses, and the projected cost of administering the drug is displayed in association with the recommended treatment.

In situations where the disease condition is caused by a microbial etiology, and the actual treatment is an antimicrobial treatment, the recommended treatment is updated in a time interval that reduces the development of antimicrobial drug resistance. For example, an antibiogram is produced using current (e.g. last 30–120 days) laboratory information about patterns of microbial susceptibility to empirical antibiotic treatment. Emerging patterns of microbial resistance to an antibiotic treatment can be quickly identified in this manner, and the ranking of recommended antibiotic treatments changed to reduce the development of antimicrobial resistance. This quick detection of emerging patterns of microbial resistance, and a prompt change in antibiotic prescribing patterns, can help prevent or reduce the establishment of fixed microbial resistance. This approach can also recognize and address such emerging patterns of resistance in relatively small geographic areas (such as cities or individual hospitals), which is a more realistic standard than the annual reports of national trends of resistance that are used at the present time.

In particularly disclosed embodiments, a clinical outcome of empirical treatment with antimicrobial drugs is stored and used to determine future recommendations for antimicrobial treatment. For example, results are stored for culture and sensitivity tests for microbial specimens taken from patients in the same geographical location, within a specified period of time (such as 120 days), and those results are used to modify the recommended treatments by recalculating an indicator of microbial resistance as each of the results is stored. The indicator of microbial resistance may be, for example, the percentage of microbial isolates that are found to be "resistant" to the recommended antibiotic, within the period of interest (e.g. the last 120 days).

The present invention also includes a computer readable medium having stored thereon a data structure, which includes a first data field containing data representing a diagnosis code, wherein each diagnosis code corresponds to a particular disease condition; a second data field containing recommended treatments indexed for each particular disease condition; and a third data field containing data about the success of each of the recommended treatments in treating the particular disease condition. During a predetermined data processing operation, one of the particular disease conditions is associated with the recommended treatments indexed for the particular disease condition, and an indicator of the success of each of the recommended treatments. For example, the recommended treatments in the second data field may be a list of antimicrobial drugs, and the data in the third data field may be an expression of microbial susceptibility in the community to the antimicrobial drugs in the second data field within a specified period of time. In addition, the data in the third data field may contain information about the cost of the drugs, or the side effects encountered with use of the drugs in a particular community.

DETAILED DESCRIPTION OF A PREFERRED EMBODIMENT

Computer System

Figure 1:
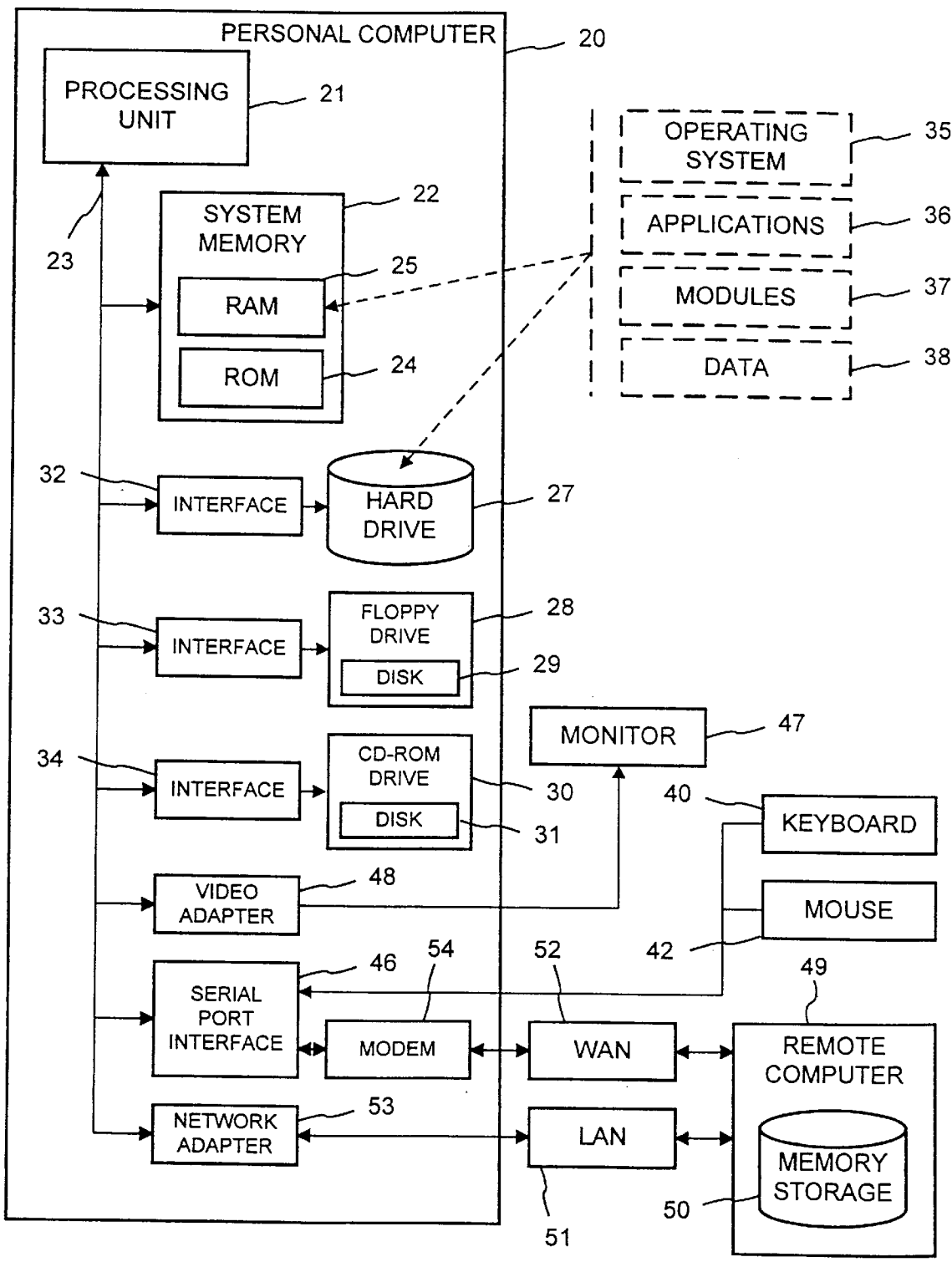
FIG. 1 is a schematic drawing illustrating a computer system in which the invention can be implemented.

FIG. 1 and the following discussion are intended to provide a brief, general description of a suitable environment in which the invention may be implemented. While the invention will be described in the general context of computer-executable instructions of a computer program that runs on a personal computer, those skilled in the art will recognize that the invention also may be implemented in combination with other program modules. Generally, program modules include routines, programs, components, data structures, etc. that perform particular tasks or implement particular abstract data types. Moreover, those skilled in the art will appreciate that the invention may be practiced with other computer system configurations, including hand-held devices, multi-processor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

With reference to FIG. 1, an exemplary system for implementing the invention includes a conventional personal computer 20, including a processing unit 21, a system memory 22, and a system bus that couples various system components including the system memory to the processing unit 21. The system bus may be any of several types of bus structure including a memory bus or memory controller, a peripheral bus, and a local bus using any of a variety of conventional bus architectures such as PCI, VESA, Microchannel, ISA and EISA, to name a few. The system memory includes a read only memory (ROM) 24 and random access memory (RAM) 25. A basic input/output system 26 (BIOS), containing the basic routines that helps to transfer information between elements within the personal computer 20, such as during start-up, is stored in ROM 24. The personal computer 20 further includes a hard disk drive 27, a magnetic disk drive 28, e.g., to read from or write to a removable disk 29, and an optical disk drive 30, e.g., for reading a CD-ROM disk 31 or to read from or write to other optical media. The hard disk drive 27, magnetic disk drive 28, and optical disk drive 30 are connected to the system bus 23 by a hard disk drive interface 32, a magnetic disk drive interface 33, and an optical drive interface 34, respectively. The drives and their associated computer-readable media provide nonvolatile storage of data, data structure, computer-executable instructions, etc. for the personal computer 20. Although the description of computer-readable media above refers to a hard disk, a removable magnetic disk and a CD, it should be appreciated by those skilled in the art that other types of media which are readable by computer, such as magnetic cassettes, flash memory card, digital video disks, Bernoulli cartridges, and the like, may also be used in the exemplary operating environment.

A number of program modules may be stored in the drive's RAM 25, including an operating system 35, one or more application programs 36, other program modules 37, and program data 38. A user may enter commands and information into the personal computer 20 through a keyboard 40 and a pointing device, such as a mouse 42. Other input devices (not shown) may include a microphone, joystick, game pad, satellite dish, scanner, or the like. These and other input devices are often connected to the processing unit 21 through a serial port interface 46 that is coupled to the system bus, but may be connected by other interfaces, such as a parallel port, game port or a universal serial bus (USB). A monitor 47 or other type of display device is also connected to the system bus 23 via an interface, such as a video adapter 48. In addition to the monitor, personal computers typically include other peripheral output devices (not shown), such as speakers and printers.

The personal computer 20 may operate in a networked environment using logical connections to one or more remote computers, such as a remote computer 49. The remote computer 49 may be a server, a router, a peer device or other common network node, and typically includes many or all of the elements described relative to the personal computer 20, although only a memory storage device 50 has been illustrated in FIG. 1. The logical connections depicted in FIG. 1 include a local area network (LAN) 51 and a wide area network (WAN) 52. Such networking environments are commonplace in offices, enterprise-wide computer networks (such as hospital computers), intranets and the Internet.

When used in a LAN networking environment, the personal computer 20 is connected to the local network 51 through a network interface or adapter 53. When used in a WAN networking environment, the personal computer 20 typically includes a modem 54 or other means for establishing communications over the wide area network 52, such as the Internet. The modem 54, which may be internal or external, is connected to the system bus 23 via the serial port interface 46. In a networked environment, program modules depicted relative to the personal computer 20, or portions thereof, may be stored in the remote memory storage device. It will be appreciated that the network connections shown are exemplary and other means of establishing a communications link between the computers may be used.

The present implementation platform of the present invention is a system implemented on an IBM compatible personal computer having at least eight megabytes of main memory and a gigabyte hard disk drive, with Microsoft Windows as the user interface and Paradox as the data base management software. The application software is written in R Base language.

Disease Classification Scheme

At the foundation of the computer system of the present invention is a classification of disease conditions that have been determined based on medical professional and health care management expertise. Each classification is correlated with a particular disease state, such as pneumonia, hypertension, meningitis, or renal failure. Each disease state is farther broken down into subcategories within the classification scheme, according to demographic and other clinical information.

One of these classification schemes is the Diagnosis Related Group (DRG). The Social Security Amendments of 1983 (Public Law 98-21) introduced a diagnosis specific prospective payment system based on the DRG, that has been incorporated into the Medicare reimbursement policies. Under the DRG system, the amount of payment for a patient hospital stay is determined by one of hundreds of government defined DRGs into which a patient hospital stay is categorized, based upon a patient diagnosis and procedures performed on the patient. Hospitals are reimbursed according to a fixed schedule without regard to actual costs to the hospital in rendering medical services to the patient. This same reimbursement policy has been extended to other health care financing entities, such as private insurance companies.

The DRGs represent a statistical, clinical classification effort to group together those diagnoses and procedures that are clinically related and have similar resource consumption. A DRG that is appropriate for a given hospital stay is selected, under the reimbursement system, by a particular set of patient attributes which include a principal illness diagnosis, specific secondary diagnoses and procedures performed. The principal diagnosis is that condition which caused the patient to be hospitalized, even though the patient may have other serious problems, which may be indicated by secondary diagnoses.

A few examples of DRGs are given in Table I. A fixed reimbursement factor is assigned to each DRG by the government. This factor determines the amount the hospital will be reimbursed for treatment of a patient who falls within the DRG, regardless of the hospital's cost or what the charges would have been for a non-Medicare patient. There are currently hundreds of DRGs that cover all patients treated under inpatient conditions. These DRGs are set forth in the regulations of the Health Care Financing Administration. The examples of DRGs shown in Table I are taken from those regulations.

The DRG code is particularly convenient to use with the computer implemented system of the present invention, because this system is designed to optimize the cost-effective utilization of medical resources. Hence the allowed cost of treating a disease can be indexed to the DRG, and provided as part of the information provided to a health care provider when making clinical decisions.

A principal magnetic disc data file that is part of the system of FIG. 1 contains a listing of all the DRGs. It is accessible by disc drive 28. The DRG file is a static computer database having one record for each DRG number.

TABLE I

SAMPLE DIAGNOSIS RELATED GROUPS (DRGs)
AS PUBLISHED IN FEDERAL REGISTER SEPTEMBER 1, 1983

| DRG | MDC | SEX | TITLE | RELATIVE WEIGHT | MEAN LOSS | OUTLIER CUTOFFS |
|---|---|---|---|---|---|---|
| 31 | 1 MED | B | CONCUSSION AGE >69 AND/OR C.C. | 0.6051 | 4.6 | 25 |
| 32 | 1 MED | B | CONCUSSION AGE 18–69 WITHOUT C.C. | 0.4519 | 3.3 | 19 |
| 33 | 1 MED | B | CONCUSSION AGE 0–17 | 0.2483 | 1.6 | 5 |
| 34 | 1 MED | B | OTHER DISORDERS OF NERVOUS SYSTEM AGE >69 AND/OR C.C. | 0.9927 | 7.1 | 27 |
| 35 | 1 MED | B | OTHER DISORDERS OF NERVOUS SYSTEM AGE <70 WITHOUT C.C. | 0.8480 | 6.2 | 26 |
| 96 | 4 MED | B | BRONCHITIS & ASTHMA AGE >69 AND/OR C.C. | 0.7996 | 6.9 | 24 |
| 97 | 4 MED | B | BRONCHITIS & ASTHMA AGE 18–69 WITHOUT C.C. | 0.7256 | 6.2 | 21 |
| 98 | 4 MED | B | BRONCHITIS & ASTHMA AGE 0–17 | 0.4275 | 3.7 | 11 |
| 261 | 9 SURG | F | BREAST PROC FOR NON-MALIG EXCEPT BIOPSY & LOC EXC | 0.7329 | 4.8 | 19 |

Another commonly used coding system for disease is the International Classification of Diseases (ICD) system, which refers to a coding system based on and compatible with the original international version of the ICD coding system provided by the World Health System. The ICD coding system is used in North America, and it classifies diseases, injuries, symptoms, medical procedures, and causes of death. One version of these codes is listed, for example, in a publication by the Commission on Professional and Hospital Activities, Ann Arbor, Mich., entitled "ICD-9-CM" dated Jan. 1, 1979. The ICD codes are divided into Disease and Procedure sections. These sections are further divided into subsections which encompass from 1–999 three digit disease or 1–99 two digit procedure code categories. Within the three digit code categories there can be an additional 1 or 2 decimal digits to divide the codes into subcategories which further define the disease manifestations and/or diagnostic procedures.

Only a portion of the ICD codes are relevant to the DRG system. The DRG system involves the coding of diagnostic and procedural information into ICD code numbers by hospitals before a patient can be assigned a DRG. It is possible that a large number of sets of ICD numbers or codes can lead to the same DRG. Table II lists the ICD codes that currently fall within each of a few of some of the DRGs that are used as examples in Table I. The disease conditions of the present invention can be indexed by a diagnosis code that corresponds to either a DRG or an ICD, although the DRG code is used in the preferred embodiment of the invention.

Table I shows seven fields of information for each of the example DRGs given. This information is published as part of the Federal regulations. The first stored item of information is the DRG number, a one to three digit number. The next item of information, shown in the second column of Table I, is the Major Diagnostic Category (MDC) in which the individual DRG falls. The specific DRGs are grouped by the Federal regulations into MDCs of related DRGs. Each MDC is defined to include the DRGs directed to diseases of different body systems, such as the lung or the Central Nervous System (CNS).

The third column of Table I identifies the sex of the patient ("M" for male, "F" for female, and "B" for a diagnosis appropriate for both sexes). The fourth item of information for each DRG maintained in the static database is shown in the third column of Table I, namely the title or textual description of the DRG. The fifth data field, shown in the fifth column of Table I, is a relative weight for each DRG, which determines the amount of relative compensation that a hospital is given for treating a patient having the disease condition indicated by the particular DRG. The column labeled "Mean LOS" refers to the mean length of stay for a patient within this DRG, while "Outlier Cutoffs" refers to the maximum length of stays in the hospital that should be allowed in accordance with the DRG.

TABLE II

SAMPLE GROUPINGS OF ICD-9CM CODES INTO DRG CATEGORIES

DRG 31, CONCUSSION AGE = 70 AND/OR C.C. PRINCIPLE DIAGNOSIS

| Code | Description |
|---|---|
| 8500 | Concussion w/o Coma |
| 8501 | Concussion - Brief Coma |
| 8502 | Concussion - Moderate Coma |
| 8503 | Concussion - Prolong Coma |
| 8504 | Concussion - Deep Coma |
| 8505 | Concussion W Coma NOS |
| 8509 | Concussion NOS |

DRG 32, CONCUSSION AGE 18–69 WITHOUT C.C. PRINCIPLE DIAGNOSIS

| Code | Description |
|---|---|
| 8500 | Concussion w/o Coma |
| 8501 | Concussion - Brief Coma |
| 8502 | Concussion - Moderate Coma |
| 8503 | Concussion - Prolong Coma |
| 8504 | Concussion - Deep Coma |
| 8505 | Concussion W Coma NOS |
| 8509 | Concussion NOS |

DRG 33, CONCUSSION AGE 0–17 PRINCIPLE DIAGNOSIS

| Code | Description |
|---|---|
| 8500 | Concussion w/o Coma |
| 8501 | Concussion - Brief Coma |
| 8502 | Concussion - Moderate Coma |
| 8503 | Concussion - Prolong Coma |
| 8504 | Concussion - Deep Coma |

Etiology and Treatment Files

Another magnetic disc data file is provided that lists the presumed etiologies of the disease state indicated by the diagnosis code. The presumed etiologies can initially be ranked in the order that they are presumed to occur in the particular disease state. This ordering of presumed etiologies is important in selecting an empirical initial treatment for a patient, for example pending the outcome of further laboratory tests or awaiting drug response. An example of an entry in this data file is illustrated in Table III, where the diagnosis code 282 corresponds to a presumed pneumonia in a patient who is older than 40 years of age, and who has underlying alcoholism, diabetes or congestive heart failure (CHF). The diagnosis code is used as a key to access other information in the database, such as presumed etiologies, suggested treatments, information about drug cost and toxicity, and other information which is organized into a record, as shown in Table III.

TABLE III

ANTIBACTERIAL THERAPY BASED ON CLINICAL DIAGNOSIS

DIAGNOSIS#: 282   PHYSICIAN:   PAGE # 1
PATIENT ID#: 6926   NAME: BOB DOLE   DATE 01-06-97
INFECTION SITE: LUNG
DIAGNOSIS: LUNG-PNEUMONIA >40 YRS W/ UNDERLYING ALC, DIA, CHF
CIRCUMSTANCES: >40 YRS W/ UNDERLYING ALCOHOLISM, DIABETES, CHF

ETIOLOGIES
1: *KLEBSIELLA PNEUMONIAE*
2: ENTEROBACTERIACEAE
3: LEGIONELLA SP.
4: C. PNEUMONIAE
5: *STAPH. AUREUS*
6:

TREATMENT
PRIMARY
1: ERYTHROMYCIN + CEFTRIAXONE
2: ERYTHROMYCIN + CEFUROXIME
3: ERYTHROMYCIN + IMPIPENEM
4: ERYTHROMYCIN + TICARCILLIN/CLAV.
5: ERYTHROMYCIN + AMPICILLIN/SULBACTAM
6:

SECONDARY
1: ERYTHROMYCIN + TMP/SMX
2: IF SPUTUM SHOWS S. PNEUMONIAE W/NO G- BACILLI THEN PEN G OK
3:
4:

OTHER
1:
2:

| ANTIBIOTIC | DOSE (MG) | INTERVAL | DAYS THERAPY | TOTAL DOSE | COST | TOXICITY |
|---|---|---|---|---|---|---|
| ERYTHROMYCIN 500 MG IV/IM ADV | 430 | 6 | 5 | 8600 | $25.56 | 0 |
| CEFTRIAXONE 1 GM IV/IM | 2150 | 24 | 5 | 10750 | 262.58 | 1 |
| CEFUROXIME 1.5 GM IV/IM | 1146 | 8 | 5 | 17200 | 355.32 | 1 |
| IMIPENEM CILASTIN 500 MG IV/IM | 537 | 6 | 5 | 10750 | 393.50 | 3 |
| TICARCILLIN 3 GM IV/IM | 4300 | 6 | 5 | 86000 | 217.78 | 3 |

TABLE III-continued

ANTIBACTERIAL THERAPY BASED ON CLINICAL DIAGNOSIS

| AMPICILLIN/SULBACTAM 3 GM IV/IM | 1720 | 6 | 5 | 34400 | 337.16 | 3 |

NOTE: This report is designed to assist physicians in antibiotic selection based on diagnosis and cost effectiveness of antibiotic therapy
IT SHOULD NOT BE CONSTRUED AS TREATMENT ADVICE
TOXICITY RATING
(1) = <2% & NOT SERIOUS
(2) = >2% & NOT SERIOUS
(3) = <2% & SERIOUS
(4) = >2% & SERIOUS The etiologies listed for this clinical presentation are those microorganisms that have historically been found to cause the disease state (pneumonia in a patient over 40 years of age with underlying alcoholism, diabetes or CHF). The organisms are preferably listed in a rank order, from the organism most commonly found to cause this disease state, to the organism least commonly found to cause the disease state:

1. *Klebsiella pneumoniae*
2. Enterobacteriaceae
3. Legionella
4. *Chlamydia pneumoniae*
5. *Staph aureus*

Historically, these etiologies have been determined based on national statistics. However, one of the advantages of the present invention is that the etiologies may be determined based on a more limited geographic location in which the infection occurs, for example the city, state, or specific hospital where the patient has been admitted and the computer system is in use. This more limited geographic focus can allow the presumed etiologies to more accurately reflect the actual incidence of such infections in the particular population found in that limited geographic location. A more accurate reflection of actual etiologies in turn allows a better empirical treatment to be selected with which to treat the patient, pending the outcome of laboratory tests that will determine the actual organism that is causing the infection. The present invention therefore allows more accurate selection of empirical antibiotic treatment that will adequately treat the infection. Earlier adequate treatment of the infection in turn results in a faster average therapeutic response of the patient to treatment, a shorter length of stay in the hospital, and improved utilization of medical resources at a reduced cost.

A characteristic of medical practice that has not been adequately addressed by past computer implemented medical treatment systems is the constantly evolving nature of medical knowledge and microbial resistance. Hence the list of common etiologies in a community will likely change over time, with the seasons of the year or the spread of infections throughout regions of the country. A fixed list of etiologies may represent an average incidence of disease over a large geographic area, while being completely inaccurate at certain times of year, or in a restricted geographic locality that has a population with different characteristics, or a microbial prevalence that is divergent from microbial populations in other geographic regions. The list of primary etiologies may therefore change as the actual incidence of microbial infections in the community changes.

The list may be changed in several ways. A therapeutics committee may change the list every few days, weeks or months to reflect new patterns of microbial infection. Alternatively, laboratory data of diagnosed causes of infection for each diagnosis code may be automatically updated as the laboratory data becomes available. For example, the number of positive cultures (those in which an organism is isolated in culture) for each of the organisms within a specified period of time (e.g. 30, 60 or 120 days) can be stored in the database, and culture results prior to the specified period of time are discarded. The number of positive cultures grown for a patient having that particular diagnosis code are then summed, and the organisms ranked from the most common (greatest number of culture proven infections with that organism) to the least common (fewest number of culture proven infections with that organism). The rank of organisms responsible for the infection covered by the DRG condition in the specified time period can then be changed to reflect the new patterns of microbial infection.

Treatment Recommendations

Another magnetic disk data file is also stored, listing proposed treatments for the particular disease state (e.g. the condition covered by the DRG or ICD code). The proposed treatments can be ranked in a preferred order. The rank order can be from most effective to least effective for the disease condition to which the file corresponds, or ranking can be performed by a weighted combination of effectiveness and cost. The treatments may be ranked in accordance with the rank of presumed etiologies. For example, if Klebsiella if the most commonly encountered etiology in the DRG classification, then the highest ranked primary treatment will be the drug which is considered to most commonly successfully treat patients infected with this microbial pathogen (erythromycin and ceftriaxone in Table III). In time, after the program gathers data about actual clinical successes of this treatment, the drug rankings may be changed if it is found that another drug or combination of drugs is more effective in the population at a particular hospital or in the particular health system where the computer system is operating.

An example of an entry in this data file is illustrated in Table III, where the diagnosis code 282 corresponds to a presumed pneumonia in a patient who is older than 40 years of age, and who has underlying alcoholism, diabetes or congestive heart failure (CHF). The treatments for this disease condition are divided into a field for primary treatments and a field for secondary treatments. The primary treatments are those treatments that are most preferred. In the given example of a pneumonia in a patient who has the specified clinical and demographic characteristics, a combination of erythromycin and ceftriaxone are ranked first, while erythromycin and cefuroxime are listed second, and erythromycin and imipenem are listed third, etc. These proposed drug treatments are ranked in this order initially based on national recommendations. However the rankings may change in time based on the results of laboratory culture and sensitivity studies in a selected geographic area (for example, the hospital or hospital system in which the patient is being treated). The antibiotics are preferably listed in a rank order, from the antibiotics most commonly found to successfully treat this disease state, to the antibiotics less commonly found to successfully treat the disease state.

In the example of Table III, which concerns an infectious disease, the treatments will be determined by laboratory culture and sensitivity results. The rankings will be based (at least in part) on the percentage of organisms for this disease state that are found to be susceptible, as measured by mean inhibitory concentration (MIC) studies, to the proposed drug treatment. A low MIC indicates that the microorganism is susceptible to the antibiotic (a low concentration of the antibiotic inhibits the organism's growth), while a high MIC indicates a microorganism is resistant to the antibiotic (a high concentration of the drug is required to inhibit the organism's growth). When reporting such MIC results, a laboratory often simply records whether an organism is "susceptible" to the antibiotic, "intermediate" in resistance, or "resistant" to a particular antibiotic. Using ceftriaxone as an example, in a standard dilution method (broth, agar, microdilution) wherein the concentration of ceftriaxone is sequentially diluted and growth of microbial growth is monitored, MIC values obtained could be interpreted using the following criteria (where MIC refers to the concentration of the antibiotic in mcg/mL in the culture medium):

| MIC (mcg/mL) | Interpretation |
| --- | --- |
| less than 16 | Susceptible |
| >16–<64 | Intermediate |
| >=64 | Resistant |

Examples of organisms having measured MIC values, and the interpretation of those values with respect to ceftriaxone, are shown below (where S is "susceptible", "I" is "intermediate" and "R" is resistant):

| Organism | MIC (mcg/mL) |
| --- | --- |
| *Staphylococcus aureus* ATCC 29213 | 1–8 (S) |
| *Escherichia coli* ATCC 25922 | 0.03–0.12 (S) |
| *Pseudomonas aeruginosa* ATCC 27853 | 8–32 (I) |

An organism that is "susceptible" to the antibiotic will usually cause an infectious condition that can be successfully treated with the antibiotic to which the organism is shown to be "susceptible" in the laboratory. The ranking of erythromycin and ceftriaxone in the first position in the treatment rankings may therefore be an indication that most organisms cultured from the sputum or blood of patients having this disease condition are found to in fact be susceptible to this drug combination. Alternatively, if different combinations of drugs have equal percentages of success (e.g. 100% rates), then the drugs can be ranked by MIC, with drugs having lower MICs being ranked higher on the list.

Also, rankings can be altered by the cost of the drugs in the combination. For example, even though the combination of erythromycin and imipenem may be slightly more effective (e.g. lower MIC for imipenem), the cost of imipenem may be much higher than the cost of ceftriaxone or cefuroxime. In that event, imipenem may be ranked as a less preferred (higher number) choice in spite of its superior efficacy.

The rankings can be made automatically by a preselected algorithm. For example, an equation can be used that weights an effectiveness factor and a cost factor, to arrive at a numerical score that is then used to order the drugs in the list. An example of such an algorithm is presented below.

Secondary treatments can also be listed in another field, as shown in Table III. These secondary treatments are listed separately from the primary treatments because as a group they have been found to be less effective against the disease condition (DRG or ICD) than the treatments in the primary treatment list. A record is stored for antibiotics that have been found to be effective against particular organisms. Table IIIA, for example, shows a record that is stored for listing antibiotics of choice against Pseudomonas aeruginosa, with an indication in parentheses following the drug indicating whether that drug is a primary "(1)" or secondary "(2)" choice.

TABLE IIIA

ANTIBIOTICS CHOICE AGAINST SELECTED ORGANISMS

```
                                                              DATE:
PATIENT ID#:   4121        6929          FIRST: TOM           LAST: SMITH
WT: 80 KG      HT: 71 IN        DOB: 11/21/56    SEX: M    DR.: DEPPER, JOEL
MICROORGANISM: PSEUDOMONAS AERUGINOSA
   INFECTION SITE: UT1,WOUNDS,HEART,GI,CNS,SEPTICEMIA    GRAM STAIN  G- RODS
PRESCRIBED THERAPY:
                              ALERNATIVE ANTIBIOTICS
     1: AZLOCILLIN (1)      8: NETILMICIN (1)         15: CIPROFLOXACIN (2)
     2: MEZLOCILLIN (1)     9: TOBRAMYCIN (1)         16: CARBENICILLIN (u)
     3: PIPERACILLIN (1)   10: TICARCILLIN/CLAV (2)   17:
     4: TICARCILLIN (1)    11: AZTREONAM (2)          18:
     5: CEFTAZIDIME (1)    12: IMPENEM (2)            19:
     6: AMIKACIN (1)       13: PIPERACILLIN/TZ (2)    20:
     7: GENTAMICIN (1)     14: CEFOPERAZONE (2)       21:
```

PIPERACILLIN 2GM IV/IM ADV                                        DRUG#:4071813
M/C: 0.          S/C: 0.      M/A: 200.    S/A: 250.    CHOOSE ONE: 0.
WT:              DAYS THERAPY: 5           TOTAL DOSE: 0    COST/MG: 0.004297   HR: 4.
INTERVAL: 6      SEV: 4       COST: $12.87       RECOMMENDED DOSE: 0.
TOXIC: 3

This record can be retrieved for infections which are believed to be caused by this organism, such as a nosocomial infection in a neutropenic patient, or a respiratory infection associated with cystic fibrosis. Table IIIA shows a display screen in which piperacillin has been selected, and the total suggested days of therapy (5) are displayed, along with the dosage interval (every six hours), the cost of each dose ($0.52) and the toxicity level of the drug (3, which indicates toxicity in less than 2% of the population, with serious clinical consequences).

Cost Information

Another feature of the present computer system is that it is able to predict the estimated cost of treating a patient with a given drug, or combination of drugs. This prediction of cost often requires additional patient specific information that is stored in the database, and is electronically retrieved for calculating the total dose and cost of a proposed drug treatment. An example of a patient record having fields useful in computing total dosages of drugs in shown in Table IV. In one field of the record is a patient A identification number, which can be used to point to the other fields in that patient record, such as the date of birth (from which patient age is calculated), weight (in both pounds and kilograms), and serum creatinine (which is a measure of renal function that is useful in predicting the pharmacokinetics of drugs), and may be used to calculate the total dose of a drug that is administered based on a dosage per unit weight of the patient.

Another important field is the identification of any drug allergies (for example an allergy to penicillin), so that any attempt to prescribe a drug that is entered in the allergy field will prompt a warning from the system that the patient is allergic to that drug.

The patient identification form is linked to a listing of DRG classifications, and the DRG classifications can be accessed from the patient identification form shown in Table IV.

retrieved and displayed on the monitor screen in association with the infection site, diagnosis and associated clinical circumstances. A matrix is then displayed, similar to the matrix shown at the bottom of Table III, in which the drugs included in the primary treatments are listed in a first column, followed by columns showing the dose (per administration), the interval (between doses), and the total days of therapy. The dose, interval and days of therapy are specific to the disease condition and the patient being treated. For example, ceftriaxone in a dose of 1 gram per day will be administered intravenously (IV) or intramuscularly (IM) for 5 days when treating pneumonia, but a single IM dose of 250 mg will be given for treating uncomplicated gonococcal urethritis, and for treatment of meningitis a daily dose of 100 mg/kg (not to exceed 4 grams) is given in divided doses every 12 hours.

The total dose is calculated by dividing 24 by the interval (to determine the number of doses administered per day), which will be multiplied by the dose and the days of therapy. The cost per unit dosage is then multiplied by the total dose to provide an estimated cost of treatment with the drug. The estimated cost of treatment for each drug in the list is then displayed in a column so that the comparative costs of each treatment can immediately be available to assist in selection of the therapy.

Once a therapy is selected, a screen (Table IVA) is displayed which calculates the total expected dose of the antibiotic, based on the weight of the patient (86 kg), the projected number of days of therapy (5 days), the interval between doses (24 hours), the cost per mg of the drug, the recommended dose, and the anticipated cost of prescribing

TABLE IV

PATIENT IDENTIFICATION FORM

```
IDENTIFICATION NUMBER: 6929
LAST NAME: SMITH
FIRST NAME: TOM
OUTPATIENT FULL NAME: SMITH TOM
DOB: 11/21/56
ADDRESS: 1256 COPELAND TERRERBONNE, OR 97760
ROOM#: 120-1
ALLERGY: PENICILLIN
SEX: M WEIGHT LBS: 178 KG: 80 HT (IN): 71 SERUM CREAT: 1.2
 DIET: REGULAR DIET
```

Once the DRG classification has been determined, the linked lists of suspected etiologies and treatments are this therapy (including nursing cost and other costs associated with administering the drug parenterally).

TABLE IVA

TREATMENT 'Y' TO REVIEW MICROBE: N __

| | |
|---|---|
| 1ST 1: ERYTHROMYCIN + CEFTRIAXONE | MICROBES |
| 2: ERYTHROMYCIN + CEFUROXIME | KLEBSIELLA |
| 3: ERYTHROMYCIN + IMPIPENEM | ENTEROBACTERIACEAE |
| 4: ERYTHROMYCIN + TICARCILLIN/CLAV. | LEGIONELLA SP. |
| 5: ERYTHROMYCIN + AMPICILLIN/SULBACTAM | C. PNEUMONIAE |
| 2ND:1 ERYTHROMYCIN + TMP/SMX | STAPH. AUREUS |
| 2: IF SPUTUM SHOWS S. PNEUMONIAE W/NO G- BACILLI THEN | |
| 3: | Weight: 75 kg |
| CEFAZOLIN (1) CEFACLOR (1) CEPHRADINE (1) CEFMETAZOLE (1) CEFOTETAN (1) | |

TABLE IVA-continued

CEFOXITIN (1) CEFUROXIME (1) CEFTAZIDIME (1) CEFTRIAZONE (1) CIPROFLOXACIN (1)
NORFLOXACIN (1) (U) AMOXICILLIN/CLAV (2) AMPICILLIN/SULB (2) TICARCILLIN/CLAV (2)
IMPENEM (2) PIPERACILLIN/TZ (2) CEPHALEXIN (2) AMIKACIN (2) GENTAMICIN (2) TOBRA
BACTRIM (2) END -0- -0- -0-

ENTER 'Y' TO REVIEW MICROBE N ACINETOBACTER SP.
CEFTRIAXONE 1 GM IV/IM                                              CODE: 4079966
M/C: 50.    S/C: 75.    M/A: 25.    S/A:40.    CHOOSE ONE: 40.
WT: 86    DAYS THERAPY: 5.    TOTAL DOSE: 17200    COST/MG: 0.024378
INTERVAL: 24    HOURS SEV: 12    HOURS: 1.    COST: $419.82    282    6928
RECOMMENDED DOSE: 3440.    MG TOXICITY: 1    ACTUAL THERAPY (=a): __

If the actual therapy selected by a physician or other health care provider is not one of the primary or secondary treatments listed in the approved treatments field, then a message is sent to the prescriber alerting him or her to this discrepancy, and asking the prescriber to justify the departure from the approved treatment. If such a justification can be made, then the non-approved therapy is allowed to continue. If no justification is provided, the prescriber is required to change the therapy to one of the approved therapies on the list. The messages to and from the prescriber can be sent in any medium, but are preferably in the form of an electronic mail message, or displayed with a patient's laboratory results stored on a computer database, which is accessed by the physician to determine the results of laboratory tests (such as culture and sensitivity studies).

Each departure from the approved therapies is recorded, and sorted by prescriber. A report can then be generated, for a given time period, of the number of departures from approved protocol therapies by each prescriber. This information can be used as an educational tool for the prescriber, or as an indicator of unwanted medical resource utilization patterns.

Drug Protocol Development for Non-Infectious Diseases

Although the example of Table III shows a list of treatments for an infectious disease (pneumonia), the computer system of the present invention can also be used to evaluate and recommend treatments for non-infectious diseases as well.

A sample screen of some DRG descriptive listings is shown in Table V, followed by a disease condition code.

TABLE V

CRANIOTOMY- AGE GREATER THAN EXCEPT FOR TRUAMA 110
CRANIOTOMY- AGE GREATER THAN EXCEPT FOR TRUAMA 111
CRANIOTOMY- AGE GREATER THAN EXCEPT FOR TRUAMA 112
CRANIOTOMY- AGE GREATER THAN EXCEPT FOR TRUAMA 113
CRANIOTOMY- AGE GREATER THAN EXCEPT FOR TRUAMA 114
TREATMENT OF CHRONIC ANGINA 115

In the illustrated example, Treatment of Chronic Angina is associated with code 115. That code may then be entered to retrieve the record shown in Table VI, which lists the approved treatments for this disease condition. This retrieved record also displays the allowable expense permitted (under Medicare guidelines) for treatment of this condition. The allowable expense entry may be an indication of either the total charge permitted for treating the patient, or the total cost of drug treatment budgeted under the relevant DRG.

TABLE VI

DRG CODE: 115
DRG ALLOWABLE EXPENSE: $454.35
DRG DESCRIPTION: TREATMENT OF CHRONIC
ANGINA
DRG DRUGS
DILTIAZEM PROPANOLOL CARDIZEM
VERAPAMIL TIMOLOL

Protocol Development and Data Flow in Hospital Environment

Figure 2:
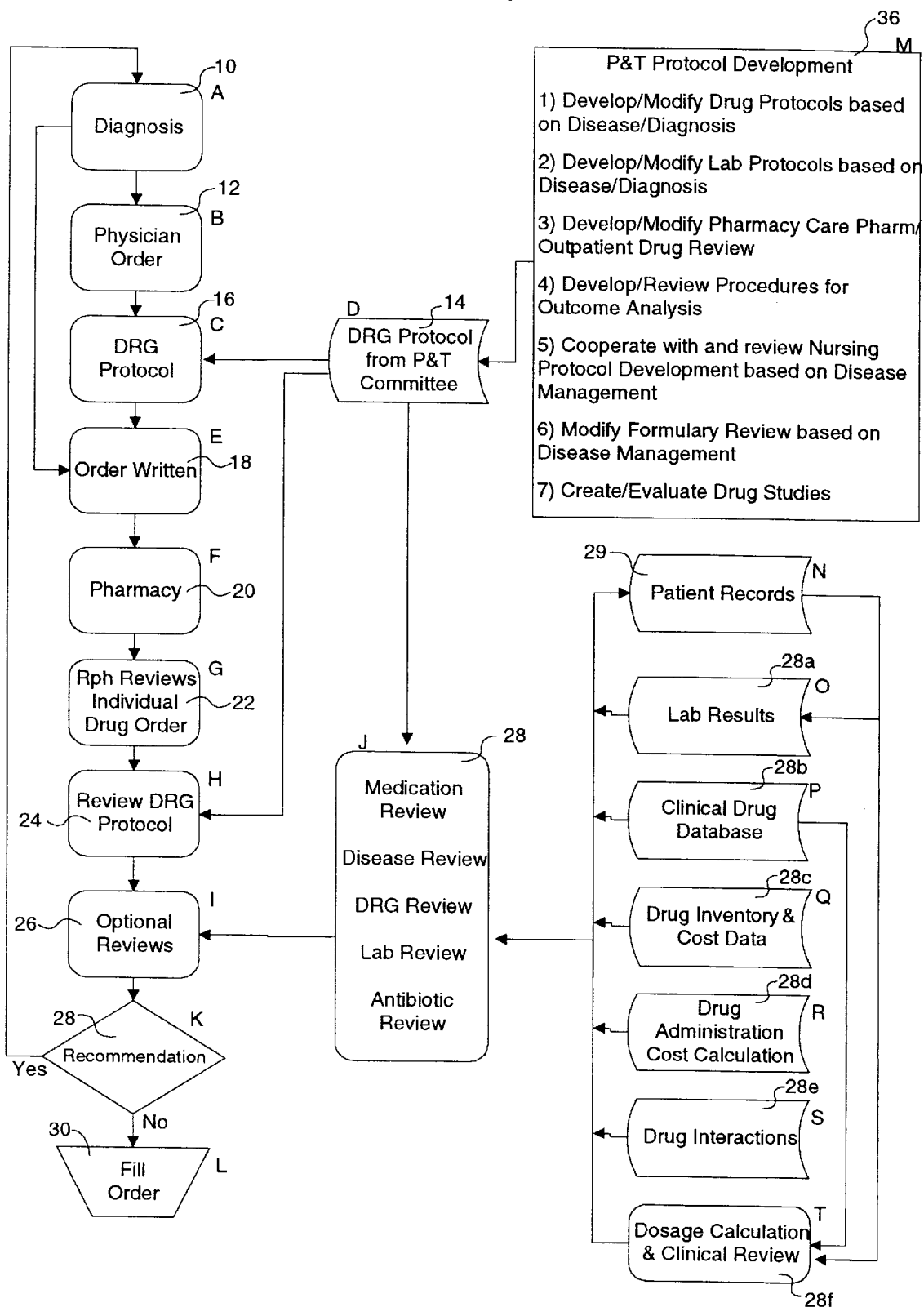
FIG. 2 is a flow chart illustrating the overall function of the computer system of the present invention.

FIG. 2 is a flow chart that illustrates the overall function of the computer implemented system of the present invention. In this method, a physician or other health care provider (which for purposes of convenience will be collectively referred to as a physician) makes a diagnosis (as shown in step 10) by traditional means, such as physical examination and laboratory data. In step 12, this diagnosis is entered into the hospital record as an order, which is then transferred to a computerized medical record system. When the diagnosis is entered into the computer (either by the physician or a clerk), the diagnosis is matched with a DRG for hospital billing purposes. Assignment of the DRG can be made by a billing specialist, the physician, or by a computer program as described in U.S. Pat. No. 5,483,413 or U.S. Pat. No. 4,667,292. Once the DRG is established, either at the time the patient is admitted to the hospital or later, a DRG protocol 14 is presented on a computer screen for the physician to review at step 16. The DRG protocol lists the recommended treatments (or the treatments approved by a hospital or other committee) for the physician to review before writing an order for treatment.

After reviewing the protocol, the physician writes an order (at step 18) to treat the patient. (Alternatively the order can be written immediately after the diagnosis is made, without first consulting the DRG protocol 14). The order often takes the form of a direction that a particular medication be given to the patient. That drug order is then communicated to the pharmacy at step 20 (for example via a hospital computer network), and the pharmacist reviews the drug order at step 22. The pharmacist also reviews the DRG protocol at step 24, and may also perform optional reviews at step 26, for example by consulting databases such as 28a (linked to patient records 29) containing patient laboratory data, clinical drug database 28b which contains drug information, drug inventory and cost database 28c, drug administration cost calculation program 28d, drug interaction database 28e (which also consults patient records 29 to detect any drug interactions with medications already prescribed to the patient which are listed in the patient record), and dosage calculation program 28f which calculates appropriate doses of medication based on patient information (such as weight and renal function retrieved from patient records 29). Dose calculations are often needed to determine the appropriate dosage of a drug according to patient weight or in view of comorbid conditions (such as renal failure). If this pharmacist review indicates that the physician order entered at step 18 varies from the DRG protocol recommendations, or if other problems are noted, then at step 28 a message 30 is sent to the physician to call attention to this variance or problem. If no such problem is noted, then the order is filled at step 32, and the prescribed treatment is given to the patient.

It will be apparent from the foregoing description that a DRG protocol must be developed as part of the process shown in FIG. 2. As the name of the protocol indicates, the protocol is developed with reference to a DRG (or an ICD or other accepted disease category). The DRG is the preferred means of categorizing the protocols, because the DRG is also associated with reimbursement information. This reimbursement information helps provide financial information to the hospital (or health care provider) which may help assist in the selection of an appropriate treatment for a DRG condition. However, the drug protocol is also a starting point from which more effective and efficient protocols can be developed, because the present invention continues to gather information about the effectiveness, side-effects and cost of the drugs on the protocol, as applied to the particular population being served by the pharmacy or hospital. This continuing collection of information is then used to modify the protocol, for example by eliminating drugs that are poorly tolerated by the population served, or are found to have an inadequate clinical effect.

The protocol development process is summarized at step 36 in FIG. 2. The protocol is developed by preparing a recommended list of drugs for each DRG condition, for example based on clinical experience and recommendations in the medical literature. Lab protocols are also devised, and set forth the laboratory tests that should be performed to effectively evaluate a patient presenting with a particular clinical condition without wasting clinical resources. A set of standards for evaluating the effectiveness of the protocol treatments and laboratory tests is also developed, and these standards help direct the collection of data that will be used in evaluating and modifying the protocols.

A specific example of information considered for each of these steps, when developing a DRG protocol for essential hypertension, is shown in Tables VII–X. The protocol development will usually involve the identification of goals or objectives of treatment, and standards for diagnosis, including clinical findings and recommended laboratory investigations (Table VII); a general statement of treatment strategies (Table VIII); and a record of pharmaceutical agents that are possible treatments along with associated costs of administering those treatments (a exemplary partial listing of some of these treatments and associated costs is shown in Table IX). Based on the information in Tables VII–IX, guidelines are prepared for selecting initial therapy (Table X), based on the clinical setting (patient history, including comorbid conditions such as angina pectoris and renal disease) in which the drug is to be used. Although not shown in the Tables, selected drug interactions with antihypertensive therapy, and known adverse drug effects, would also be taken into account in developing the protocol.

TABLE VII

INDICATIONS, GOALS, OBJECTIVES OF THERAPY

1. Goal: Treatment of hypertension to prevent morbidity and mortality associated with high blood pressure and to control blood pressure by the least intrusive means possible.
2. Indications: Systolic blood pressure of 140 mm Hg or greater and/or diastolic blood pressure of 90 mm Hg or greater.
3. Repeated blood pressure measurements will determine whether initial elevations persist and require close observation or prompt attention, or whether they have returned to normal and need only periodic remeasurement. Initial blood pressure readings that are markedly elevated (ie, a DBP of $\geq$ 120 mm Hg or an SBP of $\leq$ 210 mm Hg) or are associated with evidence of target-organ disease (heart, kidney, brain, and large arteries) may require immediate drug therapy. The timing of subsequent readings should be based on the initial blood pressure as well as previous diagnosis and treatment of cardiovascular disease and risk factors.
4. Recommendations for follow-up based on initial set of blood pressure measurements for adults:

Initial screening BP, mm Hg

| Systolic | Diastolic | Follow-up recommended |
|---|---|---|
| <130 | <85 | Recheck in 2 years |
| 130–139 | 85–89 | Recheck in 1 year |
| 140–159 | 90–99 | Confirm within 2 months |
| 160–179 | 100–109 | Evaluate or refer to source of care within 1 month |
| 180–209 | 110–119 | Evaluate or refer to source of care within 1 week |
| $\geq$210 | $\geq$120 | Evaluate or refer to source of care immediately |

5. Laboratory tests and diagnostic procedures to be performed before therapy is initiated include: urinalysis, complete blood cell count, blood glucose (fasting, if possible), potassium, calcium, creatinine, uric acid, cholesterol (total and high-density lipoprotein) and triglyceride levels; and electrocardiography.

TABLE VIII

TREATMENT

1. Treatment starts with life-style modifications: weight reduction, moderation of alcohol intake, regular physical activity, reduction of sodium intake and smoking cessation.
2. If the response is inadequate: continue lifestyle modifications and select initial pharmacological agent. Diuretics or beta-blockers are preferred because reduction in morbidity and mortality has been demonstrated. ACE inhibitors, calcium antagonists, alpha-receptor blockers and alpha-beta-blockers have not been tested nor shown to reduce morbidity and mortality.
3. If the response is inadequate: increase drug dose, or substitute another drug, or add second drug agent from a different class.
4. If the response is inadequate: add second or third agent and/or diuretic if not already prescribed.
5. Antihypertensive agents include diuretics (thiazides and related agents, loop diuretics and potassium sparing diuretics), adrenergic inhibitors (beta-blockers, beta blockers with ISA, an alpha-beta-blocker and alpha-blockers), ACE inhibitors, calcium antagonists, centrally-acting alpha-2 agonists, peripheral-acting adrenergic antagonists and direct vasodilators.
6. For thiazide and loop diuretics, lower doses and dietary counseling should be used to avoid metabolic changes. Hydrochlorothiazide or chlorthalidone is generally preferred and used in most clinical trials. The mechanism of action is decreased plasma volume and decreased extracellular fluid volume; decreased cardiac output initially, followed by decreased total peripheral resistance with normalization of cardiac output; long-term effects include slight decrease in extracellular fluid volume. Thiazides are more effective antihypertensives than loop diuretics except in patients with serum creatinine $\geq$2.5 mg/dL. Higher doses of loop diuretics may be needed for patients with renal impairment or congestive heart failure.
7. The potassium sparing diuretics' mechanism of action is increased potassium resorption. They are weak diuretics, used mainly in combination with other diuretics to avoid or reverse hypokalemia from other diuretics, should be avoided when serum creatinine $\geq$2.5 mg/dL and may cause hyperkalemia, and this may be exaggerated when combined with ACE inhibitors or potassium supplements.

TABLE VIII-continued

TREATMENT

8. The mechanism of action for the beta-blockers is decreased cardiac output and increased total peripheral resistance; decreased plasma renin activity. Atenolol, betaxolol, bisoprolol and metoprolol are cardioselective, but will also inhibit beta-2-receptors in higher doses, so all may aggravate asthma.
9. Of the beta-blockers with ISA, acebutolol is cardioselective. There is no clear advantage for agents with ISA except in those with bradycardia who must receive a beta-blocker; they produce fewer or no metablock side effects.
10. The alpha-beta-blocker labetalol has the same mechanism as beta-blockers, plus alpha-1-blockade and is possibly more effective in blacks than other beta-blockers. It may cause postural effects and titration should be based on standing blood pressure.
11. The mechanism for the alpha-blockers is blockage of postsynaptic alpha-1-receptors and vasodilation. They may cause postural effects and titration should be based on standing blood pressure.
12. ACE inhibitors block formation of angiotensin II, promoting vasodilation and decreased aldosterone; also increased bradykinin and vasodilator prostaglandins. Diuretic doses should be reduced or discontinued before starting ACE inhibitors whenever possible to prevent excessive hypotension. They may cause hyperkalemia in patients with renal impairment or in those receiving potassium-sparing agents and can cause acute renal failure in patients with severe bilateral renal artery stenosis or severe stenosis in artery to solitary kidney. In patients with serum creatinine $\geq$ 2.5 mg/dL, the dose should be reduced for benzepril, captopril, enalapril, lisiniopril, perindopril, quinapril and ramipril.
13. Calcium antagonists block inward movement of calcium ion across cell membranes and cause smooth-muscle relaxation. Dihiazem and verapamil also block slow channels in heart and may reduce sinus rate and produce heart block.
14. The dihydropyridines class of calcium antagonists are more potent peripheral vasodilators than diltiazem and verapamil and may cause more dizziness, headache, flushing, peripheral edema and tachycardia.
15. The centrally acting alpha-2-agonists stimulate central alpha-2-receptors that inhibit efferent sympathetic activity. None of these agents should be withdrawn abruptly; avoid in patients who do not adhere to treatment.
16. The peripheral-acting adrenergic antagonists guanadrel and guanethidine inhibit catecholamine release from neuronal storage sites, and Rauwolfia alkaloids act by depletion of tissue stores of catecholamines. They may cause serious orthostatic and exercise-induced hypotension.
17. The direct vasodilators hydralazine and minoxidil act by direct smooth-muscle vasodilation (primarily arteriolar). Hydralazine is subject to phenotypically determined metabolism (acetylation). For both agents, should treat concomitantly with diuretic and beta-blocker due to fluid retention and reflex tachycardia.

TABLE IX

ANTIHYPERTENSIVE AGENTS, DOSING, COSTS
(costs tailored for each facility, blank indicates not stocked)

DIURETICS

THIAZIDES AND RELATED AGENTS

1. Bendroflumethiazide 2.5–5 mg/day, freq.-qd, $_/day
2. Benzthiazide 12.5–50 mg/day, freq.-qd, $_/day
3. Chlorothiazide 125–500 mg/day, freq.-bid, $0.06/day
4. Chlorthalidone 12.5–50 mg/day, freq.-qd, $0.03/day
5. Cyclothiazide 1–2 mg/day, freq.-qd, $_/day
6. Hydrochlorothiazide 12.5–50 mg/day, freq.-qd, $0.02/day
7. Hydroflurnethiazide 12.5–50 mg/day, freq.-qd, $0.40/day
8. Indapamide 2.5–5 mg/day, freq.-qd, $0.40–0.80/day
9. Methyclothiazide 2.5–5 mg/day, freq.-qd, $0.02/day
10. Metolazone 0.5–5 mg/day, freq.-qd, $_–0.52/day
11. Polythiazide 1–4 mg/day, freq.-qd, $_/day
12. Quinethazone 25–100 mg/day, freq.-qd, $_/day
13. Trichlormethiazide 1–4 mg/day, freq.-qd, $0.05/day

TABLE IX-continued

ANTIHYPERTENSIVE AGENTS, DOSING, COSTS
(costs tailored for each facility, blank indicates not stocked)

LOOP DIURETICS

1. Bumetanide 0.5–5 mg/day, freq.-bid, $0.28–1.92/day
2. Ethacrynic acid 25–100 mg/day, freq.-bid, $0.35–0.69/day
3. Furosemide 20–320 mg/day, freq.-bid, $03.03–0.23/day

POTASSIUM SPARING DIURETICS

1. Amiloride 5–10 mg/day, freq.-qd-bid, $0.37–0.74/day
2. Spironolactone 25–100 mg/day, freq.-bid-qd, $0.04–0.16/day
3. Triamterene 50–150 mg/day, freq.-qd-bid, $0.29–0.87/day

ADRENERGIC INHIBITORS

BETA-BLOCKERS

1. Atenolol 25–100 mg/day, freq.-qd, $0.07–0.10/day
2. Betaxolol 5–40 mg/day, freq.-qd, $_/day
3. Bisoprolol 5–20 mg/day, freq.-qd, $0.76–3.04/day
4. Metoprolol 50–200 mg/day, freq.-qd-bid, $0.09–0.24/day
5. Metoprolol (extended release) 50–200 mg/day, freq.-qd, $0.36–1.06/day

TABLE X

GUIDELINES FOR SELECTING INITIAL THERAPY IN PATIENTS
WHO HAVE COMORBID CONDITIONS

CARDIOVASCULAR

1. Angina pectoris - Beta-blockers, calcium antagonists preferred, avoid direct vasodilators
2. Bradycardia/heart block, sick sinus syndrome - avoid beta-blockers, labetalol, verapamil, diltiazem
3. Cardiac failure - diuretics, ACE inhibitors preferred, avoid beta-blockers, calcium antagonists, labetalol
4. Hypertrophic cardiomyopathy with severe diastolic dysfunction - beta-blockers, diltiazem, verapamil preferred, avoid diuretics, ACE inhibitors, alpha-1-blockers, hydralazine, minoxidil
5. Hyperdynamic circulation - beta-blockers preferred, avoid direct vasodilators
6. Peripheral vascular occlusive disease - special monitoring required with beta-blockers
7. After myocardial infarction - non-ISA beta-blockers, avoid direct vasodilators

RENAL

1. Bilateral renal arterial disease or severe stenosis in artery or solitary kidney - avoid ACE inhibitors
2. Renal insufficiency (early - serum creatinine 1.5–2.5 mg/dL) - avoid potassium sparing diuretics, potassium supplements
3. Renal insufficiency (advanced - serum creatinine $\geq$ 2.5 mg/dL) - loop diuretics preferred, special monitoring required for ACE inhibitors, avoid potassium sparing diuretics, potassium supplements

OTHER

1. Asthma/COPD - avoid beta-blockers, labetalol
2. Cyclosporine-associated hypertension - Nifedipine, labetalol preferred, special monitoring required with verapamil, nicardipine, diltiazem
3. Depression - special monitoring required with alpha-2-agonists, avoid reserpine
4. Diabetes mellitus - Type I (Insulin dependent) - special monitoring required with beta-blockers, Type II - special monitoring required with beta-blockers, diuretics
5. Dyslipidemia - special monitoring required with diuretics, beta-blockers
6. Liver diseases - special monitoring required with labetalol, avoid methyldopa
7. Vascular headache - beta-blockers preferred
8. Pregnancy - preeclampsia - methyldopa, hydralazine preferred, avoid diuretics, ACE inhibitors, chronic hypertension - methyldopa preferred, avoid ACE inhibitors This information is then used to recommend laboratory protocols (which are laboratory tests that should be performed before initiating treatment for each condition), and a recommended list of drugs will then be prepared for each DRG condition. Such a list is shown in Table VI. Each medication can be ranked based on a review of the medical literature, a consideration of the adverse effects of the medication, and an analysis of the cost of treating a DRG condition with that medication. The recommended medications can be ranked, for example, on the basis of a formula that takes into account the following factors:

A=cost of medication per unit (e.g. cost of package divided by number of pills per unit)

B=Average times drug administered per day

C=Cost of administration by nursing personnel (averaged monthly)

D=Cost of dispensing by pharmacist (average time per pill/unit)

E=A+B+C+D

The medications may be ranked in order by E result, with medication regimens having lower E rankings being ranked as more preferable.

Adverse effects of drugs Q may also be taken into consideration by considering such factors as:

a=number of adverse effects reported for this medication b=pharmacy interventions required to correct medication errors c=medication errors reported Q is then calculated by Q=a+b+c. Other additional factors that are considered important to determining the adverse effects of the drug may of course be added to the E or Q calculations.

The ranking of the medications may be determined by calculating the sum R=E+Q, with the drugs being ranked from lowest score to highest score. Medications having the lowest score are considered the preferred treatments that are at least initially recommended in the DRG protocol. It is a particular advantage of the present invention that information used to calculate the numerical medication score R is continually collected and used to update the rankings. For example, changing costs of the medication will be entered into the cost equation E, which will ultimately change the ranking score R. Similarly, an increase in adverse effects detected by the data collection aspect of this program will change the Q score, which can also affect the R score. An example of a changing pattern of adverse effects could be that the racial composition of the population being treated changes, and that new racial group has a poor biochemical tolerance for the medication that is ranked first. This demographic change in the population served by the hospital (or other health care delivery organization) will be reflected in the rankings, which will change to better serve the new population.

Many DRG categories will have several protocol treatments for the DRG condition, with the treatments ranked in order of preference (usually by the R score). However, the R score alone will not always control the treatment selected. Some treatments, for example, will be inappropriate for certain racial minorities within the population served, or patients older than a certain age, or patients who suffer from a comorbid condition such as unilateral renal artery stenosis. At other times, the highest ranked treatment will fail in a particular patient. These situations can be addressed by IF statements in the ranking program.

Figure 3:
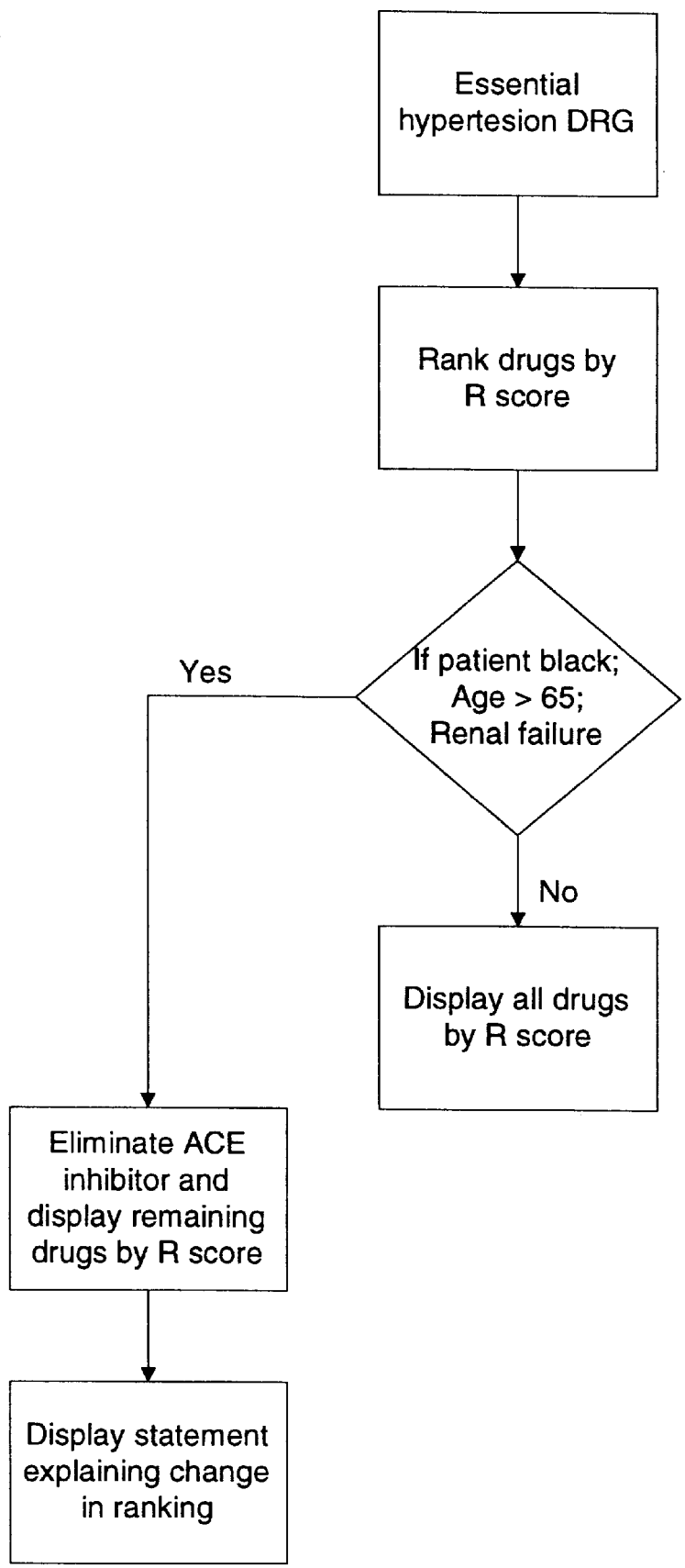
FIG. 3 is a flow chart illustrating how drugs in a protocol may be automatically reranked based on demographic information about the patient obtained from the patient record.

For example, if the DRG condition is essential hypertension and the top ranked treatments (by R score) are:

1. ACE (angiotensin converting enzyme) inhibitor
2. Diuretic
3. Beta Blocker then demographic and clinical information entered into a patient record 29 will be consulted before a final recommendation for the patient is made. As shown in FIG. 3, a IF statement would contain a series of statements that would fig establish contraindications for the use of an ACE inhibitor. Hence if the patient was black, at least 65 years of age, or diagnosed with renal failure (or renal artery stenosis), then the second ranked drug in the protocol is automatically established as the top ranked drug. A reason for this change in the ranking is then displayed to the physician or pharmacist (e.g. "ACE inhibitors should not be used in patient with renal artery stenosis"). Each subsequent drug that is then ranked first is similarly evaluated by the program for clinical contraindications. For example, if the patient with renal artery stenosis also suffers from reactive airway disease or heart block, then the beta blocker may be removed from the list (with the appropriate reason displayed).

Figure 4:
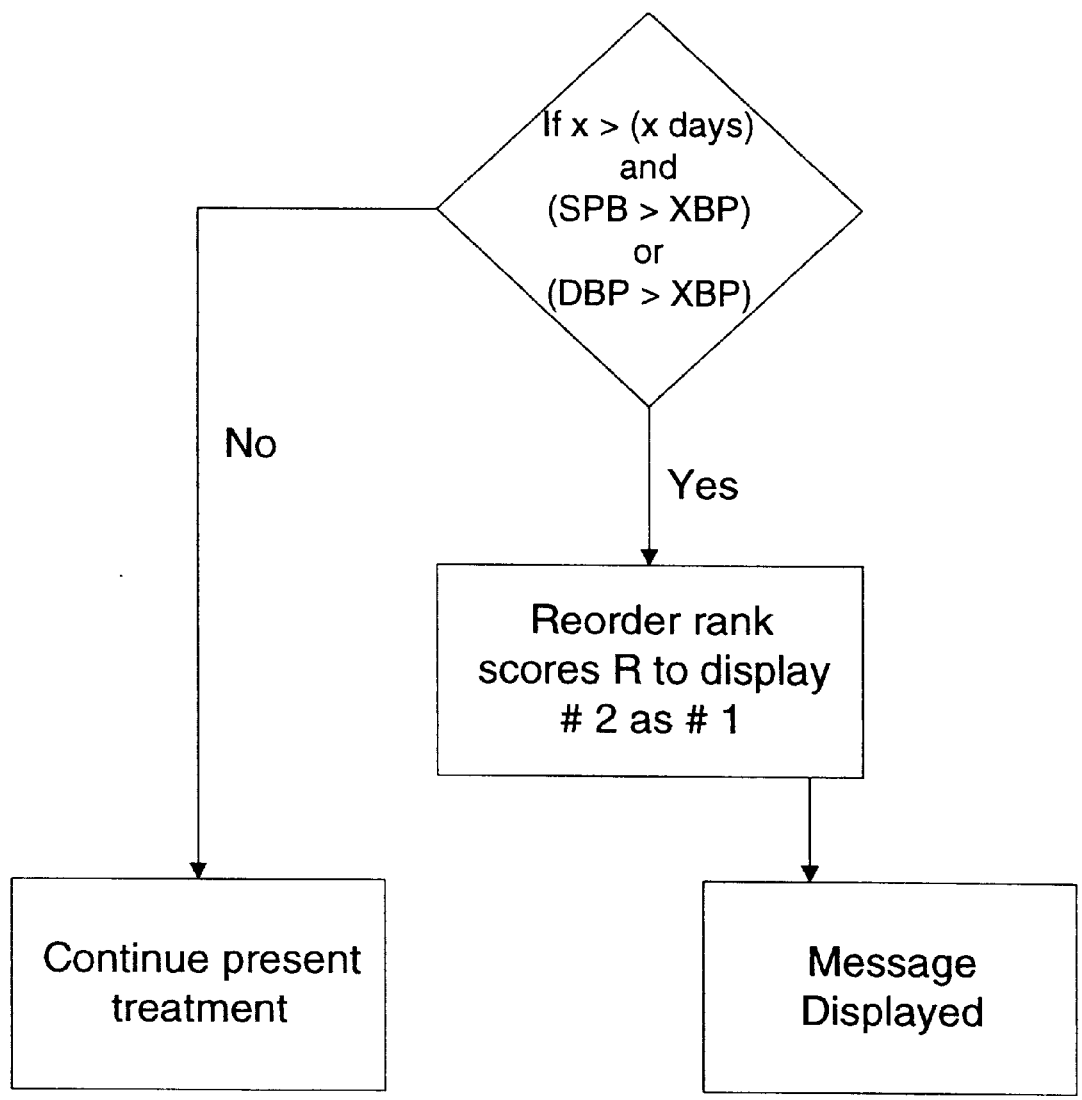
FIG. 4 is a flow chart illustrating how drugs in a protocol may be evaluated for effectiveness in a particular patient, and the ranking of the drugs changed if effectiveness is not demonstrated in accordance with the protocol.

An automatic re-ranking of the protocol treatments can also occur if the individual patient has not responded to the top ranked therapy. For example as shown in FIG. 4, if the drug in Class A fails to meet the goals established in the protocol in a preselected period of x days, then the next preferred class is automatically ranked over the previously preferred class. Hence if the patient is treated with an ACE inhibitor, and after 5 days of treatment the systolic blood pressure (SBP) is greater than 140 or the diastolic blood pressure (DBP) is greater than 90, then the rankings are reordered to rank the second preferred class of treatment (diuretic) as the top ranked therapy. The percentage of such treatment failures is also calculated, and may be used as a factor in re-ranking the therapies.

An example of a record prepared by this process is shown in Table XI, which is indexed by the DRG Heading Code 133 for Treatment of Essential Hypertension. Table XI illustrates that the DRG Total Allocation (total allowed expenditure for the hospital treatment of the condition) is displayed as part of this record to help inform the selection of drugs and other treatments that are within the allowed expenditures.

TABLE XI

DRG PROTOCOL

DRG HEADING CODE: 133    DRG TOTAL ALLOCATION: 1456.54
DRG NAME CODE: 102.44
DRG MAIN DESCRIPTION: Treatment of Essential Hypertension
    DRG SUB GROUP CODE: 1113.45
DRG SUB GROUP DESCRIPTION: Treatment of Essential Hypertension
DRG MEDICATIONS
Captopril (1) Hydrochlorothiazide(2) Propanolol(3)
Nifedipine (4) Guanabenz(5) hydralazine(6)
DRG MEDICAL REVIEW
To Prevent Morbidity and mortality. Use repeated blood pressure
measurements. Initial BP DBP>120 or SBP>120 evidence of end
organ disease require immediate therapy. See chart for
screening recommendations. Treat with life style modifications,
drugs classes includes diazides, ACE inhibitors, beta blockers,
alpha adrenergic inhibitors.

The DRG medications that are part of the protocol are then displayed in ranked order, with the rank displayed after the drug name. Captopril (an ACE inhibitor) is listed first, with the designation (1) indicating that it is the first choice according to the protocol ranking result R. Hydrochlorothiazide (a diuretic) is listed second, with the designation (2) indicating that it is the second ranked drug according to the protocol ranking R. Propranolol (a beta blocker) is listed third, with the designation (3) indicating that it is the third choice according to the ranking R. Nifedipine (a calcium channel antagonist) is similarly ranked fourth, guanabenz (a sympatholytic agent) is ranked fifth, and hydralazine (a direct vasodilator) is ranked sixth.

According to the DRG Protocol for essential hypertension, captopril would be selected as the drug of choice for this condition. If a physician orders a drug that is not listed on the protocol (such as the alpha adrenergic blocker Prazocin), or does not enter the top ranked drug, a message is sent to the physician stating that a non-protocol drug has been selected, and a justification for this variance is requested. Absent appropriate justification, the variance is not allowed, and the order is changed to the appropriate protocol drug.

If the patient is black, the protocol drugs will be automatically reranked, so that captopril (an ACE inhibitor) will be automatically eliminated from the listing (FIG. 3), because a diuretic remains the first choice therapy in these patients, and an ACE inhibitor is less likely to be cost effective. Similarly, if the patient has unilateral renal artery stenosis, which is an absolute contraindication to administration of an ACE inhibitor, then the ACE inhibitor is also automatically eliminated from the rankings.

Blood pressure readings of the patient are taken in the hospital, for example three times a day or more, to monitor response to anti-hypertensive therapy. If the protocol requires that a response to the first ranked therapy be demonstrated in three days, then the patient's blood pressure (both systolic (SBP) and diastolic (DBP) is entered in response to a prompt automatically displayed on a computer screen on the third day of hospitalization. If the SBP or DBP are above the desired levels at that time (e.g. SBP 140 or DBP 90) then the protocol drugs are reranked by eliminating the top ranked drug (captopril), and now showing the diuretic (such as hydrochlorothiazide) as the top ranked drug. A message can be sent to the prescriber noting that the protocol now has changed the rankings of the drugs, and asking if a drug change will be made. The prescriber is then given an opportunity to justify not following the protocol, and if the justification is not forthcoming, the drug will be changed to the new top ranked drug (the diuretic).

Automatic Collection of Adverse Drug Reactions

Another of the advantages of the present invention is that it can monitor adverse drug reactions to drugs as treatment progresses, and use that information to modify the DRG protocol treatments. An Adverse Drug Reaction Form can be accessed through a menu, and the menu prompts the user to identify the drug to which the adverse reaction has occurred, the class of drug to which the medication belongs, select the type of reaction that has been observed (from a list of choices), and quantify the clinical seriousness of the reaction. An example of the Adverse Drug Reaction Form is shown in Table XII.

TABLE XII

ADVERSE DRUG REACTION REVIEW FORM

| | | | |
|---|---|---|---|
| PATIENT ID#: 6893 | 6893 | LEET RUSTY | |
| PRESCRIBING PHYSICIAN: Weston, Mark | | | |
| DISCHARGE DATE: | | | |
| 1. TYPE OF REACTION: | SKIN/DERMATITIS | NAUSEA/VOMITING | ANAPHYLAXIS |
| | CARDIAC DYSRHYTHMIA | DROWINESS | |
| | OTHER-PLEASE DESCRIBE | | |
| ANSWER: SKIN/DERMATITIS | | | |
| 2. NAME AND CATEGORY OF DRUG CAUSING ADVERSE DRUG REACTION | | | |
| ANALGESIC AGENT | ANTI-SEIZURE AGENT | OTHER-PLEASE SPECIFY | |
| CARDIOVASCULAR AGENT | CNS AGENT | | |
| ANTIMICROBIAL AGENT | HYPNOTIC AGENT | | |
| CHEMOTHERAPY AGENT | ANTI-INFLAMMATORY | | |
| DRUG NAME: PENICILLIN 500 MG VK PO DRUG CLASS: | | | |
| PRESS F2 TYPE IN GENERIC DRUG NAME THEN HIT ENTER | | | |

The generic name of the drug (for example penicillin) is then entered, which causes a menu of possible penicillin preparations to be displayed. The specific drug that has caused the reaction (for example Penicillin 500 mg VK PO) is then selected from the menu (Table XIII).

TABLE XIII

PENICILLIN 2 MU IV/IM PENICILLIN
PENICILLIN 500 MG VK PO UD PENICILLIN
PENICILLIN 5 MU IV/IM PENICILLIN
PENICILLIN G BENZATHINE/PROCAINE 900/300 INJ PENICILLIN
    CHEMOTHERAPY AGENT    ANTI-INFLAMMATORY
    DRUG NAME: PENICILLIN 500 MG VK PO    DRUG CLASS:

The class of drugs (penicillin) is then either automatically retrieved, or is entered from a walk through menu by the user. A list of categories of reaction severities is then displayed, as shown in Table XII, and a category of reaction is selected by number. The menu selections vary from category 1 (reaction only anticipated but not clinically evinced) to category 4 (injury severe, not resolved prior to discharge). An example of a category 4 injury would be an anaphylactic reaction with respiratory compromise and a permanent neurological insult.

TABLE XIV

ACUITY/SEVERITY OF REACTION (PLACE A NUMBER IN THE 'ANSWER' BOX)
1. CATEGORY 1: INJURY/EFFECT OF REACTION ANTICIPATED
2. CATEGORY 2: INJURY/EFFECT MILD/TRANSIENT, RESOLVED RAPIDLY
3. CATEGORY 3: INJURY MODERATE, RESOLVED PRIOR TO DISCHARGE BUT REQUIRED SIGNIFICANT INTERVENTION OR PATIENT WAS GIVEN A DRUG TO WHICH THE PATIENT WAS KNOWN TO BE ALLERGIC
4. CATEGORY 4: INJURY SEVERE, NOT RESOLVED PRIOR TO DISCHARGE
ANSWER: 3 CATEGORY 3: INJURY MODERATE, RESOLVED PRIOR TO DISCHARGE BUT REQUIRED SIGNIFICANT INTERVENTION OR PATIENT WAS GIVEN A DRUG TO TREAT REACTION
COMPLEXITY OF CASE: SELECT ONE: 1. HIGH  3. LOW
                                 2. MODERATE
ANSWER:

As shown in Table XIV, a menu entry is also prompted for the complexity of the case, i.e. high, moderate or low. The information gathered in this part of the program is then used to modify the ranking of the protocol drugs.

In addition to actual adverse reaction information, data is also collected on clinical interventions that are required when an order contains a medication error. Clinical interventions refer to an action, usually taken by a pharmacist when reviewing an order that has been entered into the hospital record, to correct a medication error. Table XV shows a clinical intervention form displayed in accordance with the present invention, which categorizes types of medication errors that require intervention:

TABLE XV

CLINICAL INVERVENTION FORM

PATIENT ID #: 6893                           6893                          LEET RUSTY
DATE: 7/14/97  TIME: 1400  NURSING UNIT: 2N  M.D.: Weston, Mark
TYPE OF INTERVENTION: (PLEASE WRITE IN AS MANY AS APPLY)
A. INCORRECT PATIENT                    K. DUPLICATE THERAPY    T. IV/PO CONV
B. INCORRECT ADMINISTRATION SCHEDULE    L. TPN                  U. NO D/C QTY
C. ADMINISTRATION SCHEDULE CHANGE       M. INCORRECT ROUTE      V. DIRECTION
D. FAILURE TO DISCONTINUE A MEDICATION  N. NO ROUTE                CHANGE
E. ADVERSE DRUG REACTION                O. ILLEGIBLE ORDERS     W. OTHER
F. INCORRECT FREQUENCY                  P. PCA
G. INCORRECT DOSE                       Q. ALLERGY
H. MUE (SPECIFY)                        R. NO DRUG STRENGTH
I. NONFORMULARY (FREQUENCY, DOSE ROUTE) S. CONSULT
J. ROUNDS (SERVICE)
ANSWERS: 1. G INCORRECT DOSE
         2. _ _
         3. _ _
PRESS F2 AND SELECT INTERVENTION THEN PRESS ENTER In the example shown in Table XV, "G" is entered to indicate that an incorrect dose was prescribed. The user is prompted to select another screen (Table XVI), which displays a menu of interventions from which the user selects the intervention that was performed.

TABLE XVI

OUTCOME DUE TO INTERVENTION
A. MORE APPROPRIATE DOSING REGIMEN   C. FINANCIAL
B. PREVENTION OF ALLERGIC REACTION   D. OTHER
ANSWERS: 1. A MORE APPROPRIATE DOSING REGIMEN
         2. _ _
         3. _ _
RECOMMENDATION

TABLE XVI-continued

CHANGE IN DOSE RECOMMENDED
RECOMMENDATION WAS (ACCEPTED) (REJECTED): ACCEPTED
COMMENTS
TIME INVOLVED:        COST SAVINGS: $0.00      PHARMACIST:

The next screen asks for the suspected outcome without intervention, and prompts to enter one of the categories of suspected outcome, as shown in Table XVII.

TABLE XVII

SUSPECTED OUTCOME WITHOUT INTERVENTION
A. CRITICAL/LIFE THREATENING   E. ALLERGIC REACTION
B. DELAY IN THERAPY            F. OVERDOSE
C. FINANCIAL                   G. SUBTHERAPEUTIC DOSE
D. NONE                        G. OTHER
ANSWERS: 1. F OVERDOSE
         2. _ _
         3. _ _
DESCRIPTION OF SITUATION

The clinical interventions in each category are summed for each drug in the protocol, as shown in Table XVIII.

TABLE XVIII

| Viewer | |
| --- | --- |
| ADMINISTRATION SCHEDULE CHANGED | 1 |
| ADVERSE DRUG REACTION | 2 |
| ALLERGY | 15 |
| CONSULT | 6 |
| DUPLICATE THERAPY | 11 |
| FAILURE TO DISCONTINUE A MEDICATION | 9 |
| ILLEGIBLE | 2 |
| ILLEGIBLE ORDERS | 7 |
| INCORRECT ADMINISTRATION SCHEDULE | 7 |
| INCORRECT DOSE | 16 |
| INCORRECT FREQUENCY | 12 |
| INCORRECT PATIENT | 3 |
| IV/PO CONVERSION | 1 |
| NO DISCONTINUED QUANTITY | 1 |
| NO DRUG STRENGTH | 13 |
| NO ROUTE | 3 |

The number of interventions required for each drug are an indication of the potential problems that can arise in the use of the drug.

The user is also prompted to categorize the reaction as avoidable, unavoidable, or possibly avoidable, as shown in Table XIX. An avoidable reaction is one that could have been avoided based on available clinical information (drug given to patient in spite of known allergy). An example of an unavoidable reaction is an unanticipated anaphylactic reaction to a drug in a patient who had received the drug before without an adverse reaction. A example of a possibly avoidable reaction is a drug reaction in a patient who had not received the drug before, but had previously exhibited an allergy to a similar drug in the same pharmaceutical class.

TABLE XIX

MORBIDITY/MORTALITY CATEGORY: SELECT ONE
1. AVOIDABLE REACTION
2. UNAVOIDABLE REACTION
3. POSSIBLY AVOIDABLE REACTION
   ANSWER: 1 AVOIDABLE REACTION

The distribution of severity levels of the medication errors can also be displayed to further quantify the problems encountered with clinical use of the drug (Table XIX). This information is automatically collected by the computer system of the present invention, and used to change the drugs recommended in the protocol.

For example, the two cardiac glycosides digitoxin and digoxin may be available in a protocol for treating heart failure. Digoxin requires glomerular (renal) filtration as its major mode of elimination from the body, while digitoxin uses hepatic metabolism as its major mode of elimination. Hence the dose of digoxin must be reduced in patients having a creatinine clearance of 10–50, while the dose of digitoxin need not be reduced. The incidence of dosing errors may be found to be much greater with digoxin, particularly in an environment with a high percentage of patients in renal failure (such as a kidney transplant center). Hence an unacceptably high number of digoxin dosage errors may be identified in this center, which information may be used to rank digitoxin higher than digoxin. This is an example of the ability of the computer system to identify particular drug problems in a local population being served, and use that information to modify protocols to fit the particular needs of the special population.

Departure from Protocol Treatment

An example of the ability of the program to detect departures from the protocol drugs, and warn the prescriber of this departure, is illustrated in the example of treating the DRG condition "Chronic Angina." Prior to entering any drug data, the DRG code for Chronic Angina is entered, which points to the approved protocol for treating this condition, and displays it as shown in Table XX.

TABLE XX

TREATMENT OF CHRONIC ANGINA ADMINISTRATION RECORD
PNEUMONIA (>40 YRS W/UNDERLYING ALC.,DIA., CHF)

| IDENTIFICATION#: 6893 | N ROOM#: 104-1 | PHYSICIAN: | Weston, Mark |
| --- | --- | --- | --- |
| LAST NAME: LEET | FIRST NAME: RUSTY | | WT: 75 |
| DIET: | | | 22:53:58 |
| ALLERGIES: furosemide | | | |
| DIAGNOSIS: | | REPORT: | |
| DISCHARGE DATE: | ACTIVE: y NOTES: n PLEASE REVIEW DRUG TH | | |

The user is then prompted to enter the therapy selected for treating this condition, which in Table XXI (Medical Administration Record) is shown to be the ACE inhibitor captopril.

TABLE XXI

| | MESSAGE BOX |
| --- | --- |
| MEDICATION ADMINISTRATION RECORD | DUPLICATE THERAPY |

| IDENTIFICATION#: 6893 | N ROOM#: 104-1 | PHYSICIAN: | Weston, Mark |
| --- | --- | --- | --- |
| LAST NAME: LEET | FIRST NAME: RUSTY | | WT:75 |
| | | 22:53:58 | |
| CAPTOPRIL | 12.5 MG PO UD   E | | |

TABLE XXI-continued

| | | |
|---|---|---|
| CAPOTPRIL | 25 MG PO UD | REPORT: |
| CAPTOPRIL | 50 MG PO | AVTIVE: y NOTES: N PLEASE REVIEW DRUG THER |

In this example, captopril is not on the approved protocol, which causes a message (Table XXII) to be printed on the screen (or on a print out) which warns that captopril is not in the current drug listing. Current drug cost information for captopril is also displayed, as is a list of the drugs that are in the protocol for the treatment of this DRG condition (Diltiazem, Propranolol, Cardizem, Verapamil, Timolol).

A general statement about the treatment of angina pectoris (stable) will then be displayed, followed by a diagnosis statement, which for example can state that either a beta blocker or calcium channel blocker is recommended initially for monotherapy. If symptoms are not adequately controlled then a combination of the 2 or 3 classes of antianginal agents is recommended. An exception would be made for clinical

TABLE XXII

DILTIAZEM PROPPRANOLOL CARDIZEM VERAPAMIL TIMOLOL MESSAGE BOX

MEDICATION ADMINISTRATION RECORD

IDENTIFICATION#: 6893   N ROOM#: 104-1   PHYSICIAN: Weston, Mark
LAST NAME: LEET   FIRST NAME: RUSTY   WT:75
DIET:   22:53:58
ALLERGIES: furosemide   WARNING- NOT IN THE CURRENT DRUG LISTING
PLEASE REVIEW DRG BEFORE ENTERING DRUG!!
DIAGNOSIS:   PLEASE ENTER TO CONTINUE REPORT:
DISCHARGE DATE:   ACTIVE: y NOTES: N PLEASE REVIEW DRUG THER The DRG protocol can be directly accessed, for example through a pop-up menu, such as that shown in Table XXIII, by highlighting and selecting the appropriate diagnosis which is categorized by the appropriate DRG code.

TABLE XXIII

CARDIOVASCULAR -A ANGINA - UNSTABLE (CRESCENDO ANGINA)
CARDIOVASCULAR a TIMOLOL
CARDIOVASCULAR a ESMOLOL
CARDIOVASCULAR a AORTIC ARCH SYNDROME (TAKAYASU SYNDROME; PULSELESS DISEASE)
CARDIOVASCULAR a AMIODARONE HCL
CARDIOVASCULAR a AMITRIPTYLINE AND PERPHENAZINE
CARDIOVASCULAR a SOTALOL
CARDIOVASCULAR a METOPROLOL
CARDIOVASCULAR a ANGINA PECTORIS STABLE #6
CARDIOVASCULAR a DISSECTING ANEURYSM OF AORTA
CARDIOVASCULAR a LABETALOL
CARDIOVASCULAR a ANGINA PECTORIS STABLE #5 - CHRONIC ANGINA TMT#2 presentations that suggest coronary vasospasm (e.g. angina at rest), which would be treated with a calcium channel blocker. The physician or pharmacist would then be able to view current information on the best therapy for the DRG, and the drug regimens that would be followed with therapy for each of the classes of drugs. Information about each individual drug (including cost information) available from a database, can also be viewed on line in association with this information.

Another significant advantage of the computer system of the present invention is that it can display comparative drug costs for the class of drugs which the physician is considering prescribing. If an ACE inhibitor such as captopril is under consideration, for example, other drugs of the same class (angiotensin converting enzyme inhibitors) are displayed together and with their costs, so that an informed decision can be made about the best and most economical treatment. An example of a display of the comparative cost information is displayed in Table XXIV.

TABLE XXIV

IDENTIFICATION#: 6893   N ROOM#: 104-1   PHYSICIAN: Weston, Mark
LASTNAME: LEET   FIRST NAME: RUSTY   WT:75
DIET:   22:53:58
ALLERGIES: furosemide
DIAGNOSIS:   REPORT:
DISCHARGE DATE:   ACTIVE: y NOTES: N PLEASE REVIEW DRUG THER
CATAPRIL 12.   N
HYPOTENSIVE   QUINAPRIL   5MG ACE INHIBITOR $0.00
    BENAZEPRIL   10MG PO ACE INHIBITOR Y $0.97 BID
COMMENTS: GIVE 1HR A   CAPTOPRIL   12.5MG PO UD ACE INHIBITOR Y $1.02 BID
START DATE: 07/14/97   CAPTOPRIL   25MG PO UD ACE INHIBITOR Y $1.11 BID
START TIME: 8:00:00   LISINOPRIL   5MG PO UD ACE INHIBITOR Y $1.16 BID
T2: 8:00:00  T3: 8:0   LISINOPRIL   10MG PO UD ACE INHIBITOR Y $1.33 BID
T7: 8:00:00  T8: 8:0   ENALAPRIL   5MG PO UD ACE INHIBITOR Y $1.44 BID
DRUG UTILIZATION REVIE
DIAGNOSIS: CAPTOPRIL   N #DISP: 0   #INV: 0 N By comparing the cost information displayed, the prescriber will be able to determine that captopril is not the least expensive ACE inhibitor, but that it is less expensive than lisinopril or enalapril.

Another feature of the computer system is that it can automatically provide information needed for adjusting drug dosages, for example reducing the doses of renally eliminated drugs in patients who have impaired renal function. A specific example of such a calculation is determining creatinine clearance, by the equation:

$$\frac{(140-\text{age}) \times (\text{ideal body weight})}{72 \times (\text{serum creatinine in mg/dL})}$$

Laboratory data about the patient (such as serum creatinine level) is retrieved from the patient record, as is the patient age and ideal body weight. As creatinine clearance declines in renal failure, the fraction of the usual dose of a drug that can be administered also declines. The dose fraction of the drug can be calculated by the equation:

$$\left[F \times \frac{\text{patient creatinine clearance}}{120} - 1\right] + 1$$

where F is the fraction of the drug normally excreted unchanged in the urine. When F is not known, the ratio of normal half-life of the drug to half-life in renal failure can instead be used. Using these or other equations the maximum dosage for the drug of interest can be computed and displayed, as shown in Table XXV.

TABLE XXV

This patient's BSA (m2) is: 1.89692734672803
This patient's IBW is 68.4 This patient's ACTUAL WEIGHT is: 75
This patient's Creatinine Clearance is: 34.87319 Age: 63
THE MAXIMUM DOSAGE FOR THIS MEDICATION IS: 450

Alternatively, dosage adjustments for varying levels of creatinine clearance for each drug can be available in a database, from which the recommended dosage can be determined. For example, dosing of acetaminophen would be altered by increasing the interval between normal doses as renal function declines. In a patient who has a creatinine clearance of greater than 50, the normal dose is given each four hours. For a patient in whom creatinine clearance is 10–50, dosing is increased to every six hours. If creatinine clearance is less than 10, then the dosing interval is increased to every eight hours.

Similar tables can be stored for reducing the percentage of the maximum dose, for given ranges of creatinine clearance. Hence the dose of captopril may be listed as 100% if the creatinine clearance is 10 or greater, but only 50% of the dose will be calculated if the creatinine clearance is less than 10.

Outcome Analysis

One of the objectives of the present invention is to provide an evolving treatment strategy that takes into account information gathered by the program to modify treatment of a patient, or modification of the protocol for treatment of future patients. At its most basic level, outcome analysis can be provided on a case-by-case basis. For example, the pharmacy staff may review a physician's orders for treatment of a particular patient, and provide recommendations for changing the therapy. A sample form for this purpose (which may be displayed on a screen or printed out) is shown in Table XXVI.

TABLE XXVI

OUTCOMES ANALYSIS FORM 6893    6893    LEET RUSTY
PHYSICIAN: Weston, Mark    ROOM#: 104-1
DEAR DR: REQUEST
The pharmacy staff at BMH has reviewed your orders on this patient and would like to make the following recommendations for your consideration..
MEDICATION/DIAGNOSIS REVIEW
OUTCOMES SUMMARY
DO YOU WISH TO PRINT    OR FAX THIS REQUEST    (ENTRY Y OR N)

However, in a more comprehensive sense, the data collected about treatment outcomes (e.g. was blood pressure controlled within three days? did empirical treatment for pneumonia successfully treat the infection?), side-effects (e.g. anaphylaxis, hypotension, respiratory compromise), and required interventions (dosing problems, transcription errors of similarly named drugs) are used to continually evaluate and update the drugs on the protocol, and the rankings of the drugs within the protocols.

It will be appreciated from the foregoing description that the present computer system provides many advantages that have not previously been available. For the first time it gives individual hospitals or geographic localities the ability to provide rational protocols for treatment of disease in its community, and a mechanism to enforce the use of those protocols. The computer system also enables data to be collected, in the community where it is used, to assess the usefulness of that protocol in that subpopulation. This departure from standards set on an average basis, at the national level, over an average period of time, permits the best medical care to be delivered to the individual patient. The pharmacologic idiosyncracies of the population being served are identified and treatment is modified to address those particular needs. The disclosed computer system can also be used to identify emerging patterns of microbial resistance, and change antibiotic prescribing patterns before the microbial resistance becomes well established.

In view of the many possible embodiments to which the principles of this invention may be applied, it should be recognized that the illustrated embodiment is only a preferred example of the invention and does not limit the scope of the invention, which is more appropriately understood in view of the following claims:

I claim:

1. A computer implemented method for improving drug treatment for a disease condition, comprising:

storing a plurality of disease conditions by a diagnosis code, wherein each diagnosis code corresponds to a particular disease condition;

storing recommended treatments indexed for each particular disease condition;

receiving as input an actual treatment for the particular disease condition;

storing data about a clinical outcome of the actual treatment; and modifying the recommended treatments for each particular disease condition based on the data stored about the clinical outcome.

2. The method of claim 1, wherein the diagnosis code corresponds to a diagnosis related group.

3. The method of claim 2, wherein the recommended treatments are included in a protocol that also specifies laboratory tests that should be performed for the evaluation of the disease condition coded by the diagnosis related group.

4. The method of claim 1, wherein the recommended treatments are displayed with an indicator of order of preference of the treatments.

5. The method of claim 1, wherein the recommended treatment comprises administering a drug, and the method further comprises displaying comparative costs, in association with the recommended treatments.

6. The method of claim 1, wherein the recommended treatment comprises administering a drug, and the method further comprises storing costs per unit dose of drugs that are included in the recommended treatments, and storing patient specific parameters from which a predicted total required number of unit dosages of the drug are calculated, and the projected cost of administering each of the recommended treatments is calculated from the cost per unit dosage and the predicted total required number of unit dosages, and the projected cost of administering the drug is displayed in association with the recommended treatment.

7. The method of claim 1, wherein the disease condition is caused by a microbial etiology, and the actual treatment is an anti-microbial treatment, and the recommended treatment is updated in a time interval that reduces the development of anti-microbial drug resistance.

8. The method of claim 7, wherein storing data about a clinical outcome comprises generating an antibiogram that includes an indication of the success of a drug in treating the disease condition having the diagnosis code, and modifying the recommended treatment based on the antibiogram.

9. The method of claim 7, wherein storing the data about a clinical outcome further comprises ranking the drug by a combination of cost and safety.

10. The method of claim 9, wherein the cost is determined by monitoring treatment outcome results.

11. The method of claim 1, wherein the recommended treatment comprises a list of treatments in a ranked order, and modifying the recommended treatments comprises changing the rankings of the recommended treatments based on the collected data.

12. The method of claim 1, wherein the recommended treatment comprises a list of recommended antibiotic drug treatments in ranked order, and the method further comprises displaying an indicator of calculated microbial resistance to each antibiotic drug.

13. The method of claim 12, wherein storing data about a clinical outcome comprises storing the results of culture and sensitivity tests for microbial specimens taken from patients in the same geographical location where the data about clinical outcome was obtained, within a specified period of time, and modifying the recommended treatments comprises recalculating the indicator of microbial resistance as each of the results is stored.

14. The method of claim 13 wherein the antimicrobial treatment is updated by providing an indication of the susceptibility of the organism to each of the recommended treatments, in the community where the treatment is to be provided, within a period of no more than 120 days.

15. The method of claim 1, further comprising displaying projected costs of each of the recommended treatments in a display matrix to aid in the selection of the actual treatment.

16. The method of claim 1, wherein the recommended treatments are included in a protocol for the treatment of the disease condition, and the computer system collects data about the success of treatment with the protocol.

17. The method of claim 16, wherein the data about the success of treatment includes data indicating whether the treatment satisfied criteria for successfully treating the disease.

18. The method of claim 17, wherein the data about the success of treatment includes data indicating the occurrence of adverse reactions to the treatment.

19. The method of claim 1, wherein the recommended treatments are included in a protocol for the treatment of the disease condition, and the computer system alerts a prescriber if an actual selected treatment is not listed in the protocol for treatment of the disease condition.

20. A computer readable medium having stored therein instructions for performing the steps of claim 1.

21. A computer system for improving drug treatment for a disease condition, comprising:

storing a plurality of disease conditions by a diagnosis code that corresponds to a Diagnosis Related Group;

storing a protocol of a recommended treatment or treatments for each of the disease conditions;

receiving an input about an actual treatment for the disease condition;

comparing the actual treatment to the protocol of recommended treatments, and providing an indication of a departure from the protocol;

collecting data about the success of the actual treatment in treating the disease condition;

modifying the protocol in response to the data collected.

22. The computer system of claim 21, wherein the data about the success of the actual treatment comprises an indication about whether the actual treatment satisfied criteria of effectiveness provided in the protocol.

23. The computer system of claim 22, wherein the disease condition is caused by a microorganism, the actual treatment is an antibiotic, and the criteria of effectiveness is whether a microorganism in an appropriate clinical specimen from the patient was sensitive to the antibiotic.

24. The computer system of claim 22, wherein the data about success of the actual treatment further comprises data indicating the incidence of side-effects and medication errors.

25. A computer system for improving antimicrobial treatment by reducing antimicrobial resistance in a community where treatment is to be provided, comprising:

storing a plurality of microbially induced disease conditions by a diagnosis code, wherein each diagnosis code corresponds to a particular disease condition having a microbial etiology;

storing probable microbial etiologies of the disease condition;

storing recommended treatments for each particular disease condition, in ranked order;

calculating a current indicator of the treatment success of an antimicrobial agent against the particular disease condition in the community where the treatment is to be provided; and displaying the recommended treatments to assist in the selection of an actual treatment.

26. The computer system of claim 25, further comprising:

inputting the actual treatment; and storing a laboratory determined indicator of the success of the actual treatment against the organism determined to be the microbial etiology; and recalculating the current indicator of the treatment success based on cumulative data of the success of the actual treatment for the particular disease condition within a period of no more than 120 days, in the community where the treatment was provided.

27. The computer system of claim 25, further comprising inputting data that indicate the safety and effectiveness of the treatment.

28. A computer readable medium having stored thereon a data structure, comprising:

a first data field containing data representing a diagnosis code, wherein each diagnosis code corresponds to a particular disease condition;

a second data field containing recommended treatments indexed for each particular disease condition;

a third data field containing data about the success of each of the recommended treatments in treating the particular disease condition;

wherein during a predetermined data processing operation, one of the particular disease conditions is associated with the recommended treatments indexed for the particular disease condition, and an indicator of the success of each of the recommended treatments.

29. The computer readable medium of claim 28, wherein the recommended treatments in the second data field are a list of antimicrobial drugs, and the data in the third data field is an expression of microbial susceptibility in the community to the antimicrobial drugs in the second data field within a specified period of time.

30. The computer readable medium of claim 29, wherein the data in the third data field is a percentage of susceptibility of organisms causing the particular disease condition, to the antimicrobial drugs, within a period of no more than 120 days before the most recent susceptibility data.

31. A computer system comprising:

a central processing unit;

memory; and a data structure stored in memory, the data structure including:

a first data field containing data representing a diagnosis code, wherein each diagnosis code corresponds to a particular disease condition;

a second data field containing recommended treatments indexed for each particular disease condition;

a third data field containing data about the success of each of the recommended treatments in treating the particular disease condition;

wherein during a predetermined data processing operation, one of the particular disease conditions is associated with the recommended treatments indexed for the particular disease condition, and an indicator of the success of each of the recommended treatments.

* * * * *